(12) United States Patent
Brouillard et al.

(10) Patent No.: US 6,555,709 B1
(45) Date of Patent: Apr. 29, 2003

(54) AROMATIC AMIDES, THEIR PREPARATION PROCESS AND THEIR USE AS PESTICIDES

(75) Inventors: Agnés Brouillard, Villemomble (FR); Jacques Demassey, Montevrain (FR); Philippe Dutheil, Joinville le Pont (FR); John Weston, Maisons Lafitte (FR)

(73) Assignee: Hoechst Schering AgrEvo S.A., Paris (FR)

( * ) Notice: Subject to any disclaimer, the term of this patent is extended or adjusted under 35 U.S.C. 154(b) by 0 days.

(21) Appl. No.: 09/402,704

(22) PCT Filed: Apr. 7, 1998

(86) PCT No.: PCT/EP98/02014

§ 371 (c)(1),
(2), (4) Date: Oct. 7, 1999

(87) PCT Pub. No.: WO98/45252

PCT Pub. Date: Oct. 15, 1998

(30) Foreign Application Priority Data

Apr. 9, 1997 (FR) .............................. 97 04322

(51) Int. Cl.⁷ ...................... C07C 233/05; A01N 37/18
(52) U.S. Cl. ...................... 564/180; 514/617; 564/134; 564/139; 564/140
(58) Field of Search ................. 562/427, 455; 560/129; 564/84, 85, 86, 88, 162, 168, 180, 134, 138, 142; 514/535, 381, 522, 533, 534, 561, 562, 563, 602, 603, 618, 619, 617; 548/253, 415, 416

(56) References Cited

FOREIGN PATENT DOCUMENTS

| DE | 4319887 A1 | 12/1994 | |
|----|------------|---------|---|
| EP | 0 763 523 A1 | 3/1997 | |
| EP | 0763523 A1 * | 3/1997 | ......... C07C/233/55 |
| WO | WO 94/29267 | 12/1994 | |

* cited by examiner

*Primary Examiner*—Shailendra Kumar
(74) *Attorney, Agent, or Firm*—Frommer Lawrence & Haug LLP

(57) ABSTRACT

Aromatic amides, their preparation process and their use as pesticides.

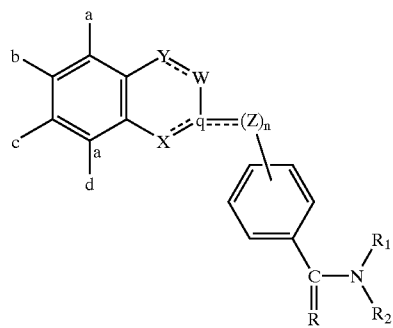

29 Claims, No Drawings

AROMATIC AMIDES, THEIR PREPARATION PROCESS AND THEIR USE AS PESTICIDES

This application is a 371 of PCT/EP98/02014, filed Apr. 7, 1998.

The present invention relates to aromatic amides, their preparation process and their use as pesticides.

A subject of the invention is the compounds of formula (I):

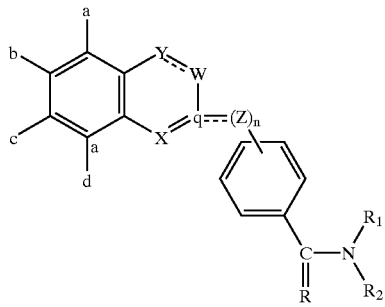

(I)

in which:
- a, b, c and d, identical to or different from one another, represent a hydrogen atom, a halogen atom, an alkyl, alkenyl or alkynyl, O-alkyl, O-alkenyl or O-alkynyl, S-alkyl, S-alkenyl or S-alkynyl radical containing up to 8 carbon atoms, optionally substituted by one or more halogen atoms, a C≡N, $NO_2$ or $NH_2$ radical, the substituents a, b, c and d being able to form between themselves rings, preferably one, which either contain or do not contain one or more, preferably one or two, hetero atoms, preferably from the group consisting of S, O and N, and which are substituted, or unsubstituted.
- Y and W, identical to or different from one another, represent both a

radical or both a

radical in which e, f and e', identical or different, represent a hydrogen atom, a halogen atom, a free, etherified or esterified hydroxyl radical, or an alkyl radical containing up to 8 carbon atoms optionally substituted by one or more halogen atoms;
- X represents a

radical or a

radical in which g, h and g', identical or different, represent a hydrogen atom, a halogen atom, a free, etherified or esterified hydroxyl radical, or an alkyl radical containing up to 8 carbon atoms optionally substituted by one or more halogen atoms, or X represents a C=O radical, an oxygen atom or a nitrogen atom, or X forms with the carbon in position 2 belonging to radical q an epoxy bridge, a cyclic hydrocarbonated radical optionally substituted by one or more halogen atoms;
- q represents a C= radical or a CD radical, in which D represents a hydrogen atom, a halogen atom or an alkyl or alkoxy radical containing up to 8 carbon atoms optionally substituted by one or more halogen atoms, or D forms with the carbon atom which carries it and one of the carbon atoms adjacent to it a carbon-carbon double bond, an epoxy radical, a cyclic hydrocarbonated radical, optionally substituted by one or more halogen atoms;
- n represents an integer varying from 0 to 8;
- Z represents a

radical in which I and k, identical or different, represent a hydrogen atom, a halogen atom, a C≡N radical, a free, etherified or esterified hydroxyl radical, an SR' radical, wherein R' is an organic rest containing up to 8 carbon atoms, preferably S-alkyl, or an alkyl radical containing up to 8 carbon atoms optionally substituted by one or more halogen atoms, or Z represents an oxygen, sulfur, nitrogen atom, a C=O or C=S radical, it being understood that if n is greater than 1, Z can take different values,
- R represents an oxygen or sulfur atom;
- $R_1$ and $R_2$, identical to or different from one another, represent a hydrogen atom, a linear, branched or cyclic, saturated or unsaturated, optionally substituted alkyl, CO-alkyl, CONH-alkyl or $CO_2$ alkyl radical contaning up to 8 carbon atoms, optionally interrupted by one or more preferably non-adjacent heteroatoms, preferably from the group consisting of N, O, S, or an optionally substituted aryl or heteroaryl radical,
- the —C—$(Z)_n$ chain is fixed in position 3 or 4 of the benzamide, the dotted lines representing one or more optional double bonds, in all their possible isomeric forms as well as their mixtures.

By compound of formula (I) are designated all the geometric isomers and stereo-isomers taken individually or in a mixture.

In the definition of substituents:
- alkyl preferably represents a methyl, ethyl, propyl, isopropyl, butyl, isobutyl, n-pentyl, isopentyl, cyclopropyl, cyclobutyl or cyclopentyl radical,
- alkenyl preferably represents a vinyl, 1-propenyl, 2-methyl 2-propenyl or isopropenyl radical,
- alkynyl preferably represents an ethynyl, 1-propynyl, 2-propynyl or pent-2-ene-4-enyl radical,
- halogen preferably represents a fluorine, chlorine, bromine or iodine atom,
- aryl preferably represents a carbocyclic aromatic group containing 4 to 10 carbon atoms, particularly preferably a phenyl, naphthyl, dihydronaphthyl, tetrahydronaphthyl, indanyl or indenyl radical, a heterocyclic radical is preferably a heteroaryl radical or a saturated or unsaturated 3 to 8 membered ring comprising one, two three or four heteroatoms from the group consisting of N, O and S.

heteroaryl is preferably a 3 to 7 membered aromatic ring comprising one, two, three or four heteroatoms from the group consisting of N, O and S, particularly preferred thienyl, furyl, pyrrolyl, imidazolyl, pyrazolyl, pyridyl, pyrazinyl, pyrimidinyl, pyridazinyl, isothiazolyl, isoxazolyl, oxazolyl, thiazolyl, oxadiazolyl and tetrazinyl Particularly preferred heterocyclic radicals are a thienyl, furyl, pyrannyl, pyrrolyl, 2H-pyrrolyl, imidazolyl, pyrazolyl, pyridyl, pyrazinyl, pyrimidinyl, pyridazinyl, isothiazolyl, isoxazolyl, furazanyl, thiazolyl, oxazolyl, pyrrolidinyl, pyrrolinyl, imidazolidinyl, pyrazolinyl, piperidyl, piperazinyl, morpholinyl, izapinyl, thiazinyl, tetrazinyl, oxathiolanyl or thiadiazinyl radical.

When the aryl or heterocyclic radical is substituted, it is preferably substituted by one or more substitutents chosen in particular from halogen atoms, alkyl or alkoxy radicals containing up to 8 carbon atoms, or methylenedioxy, difluoromethylenedioxy, tetrafluoro ethylenedioxy, cyano, nitro, cyanato, thiocyanato, pentafluorothio or fluorosulfonyl groups.

Etherified or esterified preferably means etherified with a linear or branched $C_1$–$C_8$-alkyl group or esterified with a ($C_1$–$C_8$)-carboxylic acid.

If any of the substituents a–d form a ring it is preferably a 4 to 8 membered ring which is preferably monounsaturated (due to fusion with the naphthyl group) and is carbocyclic or contains preferably one or two heteroatoms from the group consisting of N, O and S.

If Z is O, N, or CO, CS and n is greater then 1 it is preferred that heteroatoms are not adjacent to each other and CO, CS are not adjacent to each other.

It goes without saying that x, q and Z have to be chosen in a way that a tetravalent carbon at q results.

Particularly preferred are compounds of formula (I) in which Y represents a —$CH_2$— radical, those in which Y and W represent a CH radical and together form a double bond in position 3(4), those in which W represents a $CH_2$ radical, those in which q and X represent a CH= radical and together form a double bond, those in which q represents a CH or C= radical, those in which X represents a CH, a $CH_2$, a CHOH or a CO radical, those in which Z represents a $CH_2$ a CHF, a CHOH or a $COOCH_3$ radical, those in which n represents the number 1, those in which R represents an oxygen atom, those in which $R_1$ represents a hydrogen atom, those in which $R_2$ represents an alkyl radical containing up to 8 carbon atoms or a phenyl radical optionally substituted by one or more halogen atoms and/or one or more linear or branched alkyl radicals containing up to 8 carbon atoms in particular in which $R_2$ represents an alkyl radical containing up to 6 carbon atoms and in particular an isobutyl radical or a 2-methylphenyl radical, those in which at least one of substituents a, b, c and d represents a halogen atom, ($C_1$–$C_8$) alkyl or ($C_1$–$C_8$) alkoxy for example those in which two of the substituents a, b, c and d represent a chlorine or bromine atom, the compounds of formula (I) in which two of the substituents a, b, c and d represent a hydrogen atom.

In particular a subject of the invention is the compounds the preparation of which is given hereafter in the experimental part and quite particularly the compounds of Examples A, B, C, D, E, F, G, H, I, J, K, L and M.

The compounds of formula (I) can be used to combat harmful organisms such as arthropods, for example insects and acaridae, and helminths, for example nematodes, or molluscs, for example slugs. Therefore a subject of the present invention is a process for combating arthropods and/or helminths and/or molluscs, which comprises the administration to the arthropods and/or helminths and/or molluscs, or to their environment, of a quantity of a compound of formula (I) which is sufficient to destroy the harmful organism. Also a subject of the present invention is a process for combating and/or eradicating infestations by arthropods and/or helminths and/or molluscs of animals (including humans) and/or of plants (including trees) and/or stored products, which comprises the administration to the animal or to the locality of an effective quantity of a compound of formula (I). A subject of the invention is also the compounds of formula (I) to be used in human and veterinary medicine, in public health and/or in agriculture for combating harmful arthropods and/or helminths.

The compounds of formula (I) are particularly valuable in the protection of standing crops, forage crops, crops in plantations, in greenhouses, in orchards and in vineyards, of ornamental plants and trees in plantations and forests, for example cereals (such as corn, wheat, rice, sorghum), cotton, tobacco, vegetables and salad vegetables (such as beans, cabbages, cucurbitaceae, lettuces, onions, tomatoes and peppers), food crops (such as potatoes, sugar beet, peanuts, soya, oilseed rape), sugar cane, meadows and forage (such as corn, sorghum, alfalfa), plantations (such as those producing tea, coffee, cocoa, banana, palm oil, coconut, rubber, spices), orchards and tree plantations (such as those producing stone fruits and pome fruit, citrus fruits, kiwis, avocados, mangoes, olives and walnuts), vines, ornamental plants, flowers and bushes in greenhouses and in gardens and parks, forest trees (both deciduous and evergreen) in forests, plantations and nurseries. They are also valuable in the protection of timber (standing, felled, processed, stored or in buildings) against attack from wood wasps (for example Urocerus) or coleopterous insects (for example scolytidae, platypodidae, lyctidae, bostrichidae, cerambycidae, anobiidae) and termites.

They can be used in the protection of stored products, such as grains, fruits, nuts, spices and tobacco, whether whole, ground or converted into products, against attack from mites, coleopterous insects and weevils. Stored animal products such as skins, furs, wool and feathers, in natural or processed form (for example rugs or textile materials) can also be protected against attack from mites and coleopterous insects; similarly meat and fish can be protected against attack from coleopterous insects and flies.

The compounds of general formula (I) are particularly useful for combating arthropods, helminths or molluscs, which are harmful to man and domestic animals, or spread or are carriers of diseases affecting the latter, for example those which have been described above, and more particularly for combating ticks, mites, lice, fleas, midges and flies which cause bites and are harmful.

The invention also relates to the use of the compounds of formula (I) as defined previously, as pesticides in particular as insecticides, aracides and nematicides in the protection of crops in particular rice and cotton crops, or for the treatment of premises for storing said crops and in particular as insecticides and aracides in domestic or public premises.

The compounds of formula (I) can be used to these ends by the application of the compounds as they are, or in a diluted form, in a known manner, in the form of dips, sprays, mists, lacquers, foams, powders, dusting products, aqueous suspensions, pastes, gels, shampoos, ointments, combustible solids, spray pads, combustible coils, baits, food additives, wettable powders, granules, aerosols, emulsifiable concentrates, oily suspensions, oily solutions, pressurized sprays, impregnated articles, lotions or other standard compositions well known to a person skilled in the art. Concentrates for dips are not used as they are, but diluted with water, and the animals are immersed in a dipping bath containing the dipping product. Sprays can be applied by hand, or by means of a spray lance or frame. The animal, the ground, the plant or the surface can be saturated with the spray using a high volume application, or coated superficially by spraying with a light or very low-volume application. Aqueous suspensions can be applied to the animal in the same manner as sprays or dips. Dusting products must be distributed via a powder applicator or, in the case of animals, be incorporated in perforated bags fixed to trees or poles. Pastes, shampoos and ointments can be applied by hand or spread on the surface of an inert material against which the animals rub themselves and thus transfer the product onto their skin. Lotions are distributed as low-volume amounts of liquid on the backs of animals, so that all or most of the liquid remains on the animals.

The compounds of formula (I) can be presented as ready-to-use compositions for use on plants, animals or surfaces, or in the form of compositions which need to be diluted before use, but both types of compositions contain a compound of formula (I) intimately mixed with one or more excipients or diluents. The excipients can be liquid, solid or gaseous, or can contain mixtures of such substances, and the compound of formula (I) can be present in a concentration of 99 to 0.025% w/v., according to whether the composition needs a stronger or weaker dilution. Dusting products, powders and granules contain the compound of formula (I) intimately mixed with a pulverulent solid inert excipient, for example suitable clays, kaolin, bentonite, attapulgite, adsorbent carbon black, talc, mica, chalk, gypsum, tricalcium phosphate, powdered cork, magnesium silicate, vegetable excipients, starch and diatomaceous earths. These solid compositions are in general prepared by impregnating the solid diluents with solutions of the compound of formula (I) in volatile solvents, by evaporating the solvents and, if appropriate, grinding of the products to obtain powders and, if desired, by granulating, compacting or encapsulating the products.

The sprays of a compound of formula (I) can contain a solution in an organic solvent (for example those mentioned above) or an emulsion in water (dipping or spraying), prepared on site from an emulsifiable concentrate (otherwise known as oil miscible with water), which can also be used for dipping. The concentrate preferably contains a mixture of the active ingredient, with or without organic solvent, and one or more emulsifiers. Solvents can be present in very variable quantities, but preferably in a quantity of 0 to 90% w/v of the composition, and can be chosen from kerosene, ketones, alcohols, xylene, aromatic naphtha, and other solvents known for use in compositions. The concentration of emulsifiers can be very variable, but is preferably in the range of 5 to 25% w/v, and the emulsifiers are advantageously non-ionic surfactants, in particular polyoxyalkylenic esters of alkylphenols and polyoxyethylenic derivatives of hexitol anhydrides or anionic surfactants, in particular sodium laurylsulfate, fatty alcohol ethersulfates, the sodium and calcium salts of alkylarylsulfonates and alkylsulfo-succinates.

The cationic emulsifiers are in particular benzalkonium chloride and quaternary ammonium ethylsulfates.

The amphoteric emulsifiers are in particular carboxymethylated oleic imidazoline and alkyldimethyl-betaines.

Vaporization wicks normally contain a mixture of cotton and cellulose compressed into a pad, e.g. of approximately 32 mm by 22 mm by 3 mm, treated with, normally, up to 0.3 ml of a concentrate which contains the active ingredient in an organic solvent and optionally an anti-oxidant, a coloring agent and a perfume.

The insecticide may be vaporized by using a heat source, such as an electrically-powered device for heating the wicks.

The combustible solids normally contain sawdust and a binder mixed with the active ingredient and used in the form of molded strips (usually in coils). A coloring agent and a fungicide can also be added.

The wettable powders contain an inert solid excipient, one or more surfactants, and optionally stabilizers and/or anti-oxidants.

The emulsifiable concentrates contain emulsifying agents and often an organic solvent, such as kerosene, ketones, alcohols, xylenes, aromatic naphtha and other known solvents.

The wettable powders and emulsifiable concentrates normally contain 5 to 95% by weight of the active ingredient and are diluted, for example with water, before use.

The lacquers contain a solution of the active ingredient in an organic solvent, together with a resin and optionally a plastizer.

Dips can be prepared not only from emulsifiable concentrates, but also from wettable powders, dips based on soap and aqueous suspensions containing a compound of formula (I) intimately mixed with a dispersing agent and one or more surfactants.

The aqueous suspensions of a compound of formula (I) can include a suspension in water together with suspension agents, stabilizers or other agents. The suspensions or solutions can be applied as they are or in a form diluted in a known manner.

The ointments (or greases) can be prepared from vegetable oils, synthetic esters of fatty acids or lanolin, together with an inert base such as soft paraffin. A compound of formula (I) is preferably distributed uniformly throughout the mixture, in solution or in suspension. Ointments can also be obtained from emulsifiable concentrates by dilution of the latter with an ointment base.

The pastes and shampoos are also semi-solid compositions in which a compound of formula (I) can be present in uniform dispersion in a suitable base such as soft or liquid paraffin, or in a non-fat base with glycerol, a glue or a suitable soap. Since the ointments, shampoos and pastes are normally applied without any other dilution, they must contain the appropriate percentage of the compound of formula (I) required for the treatment.

Aerosol sprays can be prepared in the form of a simple solution of the active ingredient in the aerosol propellant and the co-solvent, such as a halogenated alkane and the above-mentioned solvents, respectively. The lotion compositions can be presented as a solution or a suspension of a compound of formula (I) in a liquid medium. A bird or mammalian host can also be protected against infestation by acarid ectoparasites by wearing a manufactured product in molded plastic of suitable form which is impregnated with a compound of formula (I). These manufactured products include collars, ear tags, bands, sheets and ribbons fixed in an adequate manner to the appropriate part of the body. Advantageously, the plastic material is a poly(vinyl chloride).

Therefore, a subject of the invention is in particular a composition containing:

a) a compound of formula (I) as defined previously,
b) inert excipients suitable for use as pesticides of said product of formula (I),
a composition containing:
   a) a compound of formula (I) as defined previously,
   b) inert excipients suitable for use in the veterinary field of said product of formula (I)
and a compound of formula (I) as defined previously, for the implementation of a treatment method for the human or animal body which comprises applying a pharmaceutically acceptable formulation of said compound to said body.

The compounds of formula (I) are also useful in the protection and the treatment of plant species, in which case an effective insecticide, acaricide, molluscide or nematocide quantity of the active ingredient is applied. The application rate will vary according to the chosen compound, the nature of the composition, the method of application, the type of plant, the density of plantation, the probable infestation, and other factors, but, in general, a suitable application rate for agricultural crops is in the range of 0.001 to 3 kg per hectare, and preferably between 0.01 and 1 kg per hectare. Typical compositions for agricultural use contain between 0.0001% and 50% of a compound of formula (I) and, advantageously, between 0.1 and 15% by weight of a compound of formula (I).

The concentration of the compound of formula (I) for an application on an animal, in premises or in outside areas varies according to the chosen compound, the interval between treatments, the nature of the composition and the probable infestation, but, in general the compound must be contained in the composition applied in a quantity of 0.001 to 20.0% w/v and preferably 0.01 to 10% w/w. The quantity of compound deposited on an animal varies according to the application method, the size of the animal, the concentration of the compound in the composition applied, the dilution factor of the composition and the nature of the composition, but is generally in the range of 0.0001% to 0.5% w/w, except for undiluted compositions, such as lotion compositions which are in general deposited at a concentration in the range of 0.1 to 20.0%, and preferably 0.1 to 10%. The quantity of compound to be applied on stored products is in general in the range of 0.1 to 20 ppm. Sprays can be applied in areas so as to obtain an initial average concentration of 0.001 to 1 mg of compound of formula (I) per $m^3$ of treated area.

The ointments, greases, pastes and aerosols are usually applied at random, as described above and concentrations of 0.001 to 20% w/v of a compound of formula (I) in the compound applied can be used.

The compounds of formula (I) are particularly active against lipidoptera such as *Spodoptera littoralis, Heliothis virescens, Plutella xylostella*, against coleoptera such as *Leptinotarsa decemlineata* and *Phaedon cochleariae.*

The compounds of formula (I) are thus useful for combating arthropods, for example insects and acaridae, in any environment in which they are harmful, for example in agriculture, in breeding, in public health and in domestic situations.

The harmful insects are in particular members of the orders of coleoptera (for example Anobium, Ceutorrhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), lepidoptera (for example Ephestia, Mamestra, Earias, Pectinophora, Ostrinia, Trichoplusia, Pieris, Laphygma, Agrotis, Amathes, Wiseana, Tryporysa, Diatraea, Sparganothis, Cydia, Archips, Plutella, Chilo, Heliothis, *Spodoptera littoralis, Helrotuis virescens*, Spodoptera or Tineola spp.), diptera (for example Musca, Aedes, Anopheles, Culex, Glossina, Simulium, Stomoxys, Haematobia, Tabanus, Hydrotaea, Lucilia, Chrysomyia, Callitroga, Dermatobia, Gasterophilus, Hypoderma, Hylemyia, Atherigona, Chlorops, Phytomyza, Ceratitis, Liriomyza and Melophagus spp.), phthiraptera (Mallophaga, for example Damalina spp. and Anoplura, for example Linognathus and Haematopinus spp.), hemiptera (for example Aphis, Bemisia, Phorodon, Aeneolamia, Empoasca, Parkinsiella, Pyrilla, Aonidiella, Coccus, Pseudococcus, Helopeltis, Lygus, Dysdercus, Oxycarenus, Nezara, Aleyrodes, Triatoma, Psylla, Myzus, Megoura, Phylloxera, Adelges, Nilaparvata, Nephrotettix or Cimex spp.), orthoptera (for example Locusta, Gryllus, Schistocerca or Acheta spp.), dictyoptera (for example Blattella, Periplaneta or Blatta spp.), hymenoptera (for example Athalia, Cephus, Atta, Solenopsis or Monomorium spp.), isoptera (for example Odontotermes and Reticulitermes spp.), siphonaptera (for example Ctenocephalides or Pulex spp.), thysanura (for example Lepisma spp.), dermaptera (for example Forficula spp.), psocoptera (for example Peripsocus spp.) and thysanoptera (for example *Thrips tabaci*).

Harmful acaridae are in particular ticks, for example the members of the following genera: Boophilus, Ornithodorus, Rhipicephalus, Amblyomma, Hyalomma, Ixodes, Haemaphysalis, Dermacentor and Anocentor, and acaridae and mites such as Acarus, Tetranychus, Psoroptes, Notoednes, Sarcoptes, Psorergates, Chorioptes, Eutrombicula, Demodex, Panonychus, Bryobia, Eriophyes, Blaniulus, Polyphagotarsonemus, Scutigerella and Oniscus spp.

Nematodes which attack large plants and trees in agriculture, in forestry and in horticulture, either directly, or by spreading bacterial, viral, mycoplasmal or fungal diseases of plants, are in particular root node nematodes, such as Meloidogyne spp. (for example *M. incognita*); cyst nematodes, such as Globodera spp. (for example *G. rostochiensis*); Heterodera spp. (for example *H. avenae*); Radopholus spp. (for example *R. similis*); grassland nematodes, such as Pratylenchus spp. (for example *P. pratensis*); Belonolaimus spp. (for example *B. gracilis*); Tylenchulus spp. (for example *T. semipenetrans*); Rotylenchulus spp. (for example *R. reniformis*); Rotylenchus spp. (for example *R. robustus*); Helicotylenchus spp. (for example *H. multicinctus*); Hemicycliophora spp. (for example *H. gracilis*); Criconemoides spp. (for example *C. similis*); Trichodorus spp. (for example *T. primitivus*); tusk nematodes, such as Xiphinema spp. (for example *X. diversicaudatum*), Longidorus spp. (for example *L. elongatus*); Hoplolaimus spp. (for example *H. coronatus*); Aphelenchoides spp. (for example *A. ritzemabosi, A. besseyi*); and bulb nematodes, such as Ditylenchus spp. (for example *D. dipsaci*).

The compounds of the invention can be combined with one or more other active pesticides constituents (for example pyrethroids, carbamates and organophosphates) and/or with attractants, repellents, bactericides, fungicides, nematocides, anthelminthics and similar products. Furthermore, it has been observed that the activity of the compounds of the invention can be improved by the addition of a synergic or potentiating agent, for example a synergic agent of the class of oxidase inhibitors, such as piperonyl-butoxide, or propyl 2-propynylphenyl phosphonate, by the addition of a second compound of the invention or a pyrethroid pesticide. When an oxidase-inhibiting synergic agent is present in a composition of the invention, the ratio of the synergic agent to the compound of formula (I) is in the range of 25:1 to 1:25, for example approximately 10:1.

Stabilizers used to prevent any chemical decomposition of the compounds of the invention are in particular, for example, anti-oxidants (such as tocopherols, butylhydroxyanisole and butylhydroxytoluene), vitamin C (ascorbic acid) and oxygen trapping agents (such as epichlorhydrin) similarly organic or mineral bases, for example trialkylamines, such as triethylamine, which can act as basic stabilisers and trapping agents.

The compounds of the present invention have increased pesticide properties and photostability and/or a reduced toxicity for mammals.

A subject of the invention is also a preparation process for the compounds of formula (I), wherein a compound of formula (II):

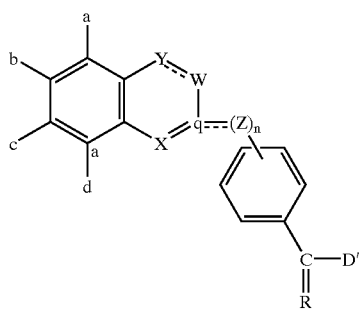

in which a, b, c, d, X, Y, W, Q, Z, n and R retain their previous meaning and D' represents a hydroxy radical, a halogen atom, an alkoxy group containing up to 4 carbon atoms or a —P(O)(Oφ)NHφ group in which φ represents a phenyl group, is subjected to the action of a compound of formula (III):

in which $R_1$ and $R_2$ retain their previous meaning in order to obtain the corresponding compound of formula (I), which is modified, if desired, in order to obtain another product of formula (I).

The products of formula (I) thus obtained can be, if appropriate, separated into their optically active isomers.

The products of formula (II) are prepared, for example, according to processes described hereafter in the experimental part, starting, e.g., from products described by M. Elliott et al., Pest. Sce 1989, 26199 (called ref. 1 in the experimental part), or by L. A. Cornelius et al., Syn. Comm. 1994, 24 (10) 2777 (called hereafter ref. 2), or starting from products prepared according to methods indicated by these authors.

Separation of the isomers can be carried out according to methods known to a person skilled in the art for example by crystallization or by chromatography.

The amidification reaction is in general carried out at a temperature comprised between −25° C. and 150° C. in an anhydrous and aprotic solvent such as ether, dichloromethane, toluene or benzene.

Workup and purification can be carried out by routine methods well known to s.o. skilled in the art.

The compounds of formula (II) used as starting material are new and are in themselves a subject of the present invention.

The disclosures in French patent application No. 97 01 541 from which this application claims priority, and in the abstract accompanying this application are incorporated herein by reference.

The following examples illustrate the invention without however limiting it.

EXAMPLE 1

4-[(6-Methoxy-3,4-dihydro-2-naphthalenyl)methyl]-N-(2-methylphenyl)benzamide 0.14 ml of orthotoluidine was added at 20° C. to a solution containing 0.65 ml of a 2M solution of trimethyl-aluminium in hexane and 5 ml of toluene. The solution obtained was agitated for 15 minutes at 20° C. and 308 mg of the product of preparation 6 in solution in 20 ml of toluene was added. The reaction medium was taken to reflux for three hours, the temperature was then taken to 20° C. and the reaction medium was treated with a solution of sodium acid phosphate. Extraction was carried out with methylene chloride followed by washing with a normal solution of hydrochloric acid, drying and concentrating. 420 mg of a product was obtained which was chromatographed on silica eluting with a heptane/dioxan mixture (7/3). In this way 351 mg of sought product was obtained.

M.p.=162° C.

EXAMPLE 2

4-[(5,8-Dibromo-2-naphthalenyl)methyl]-N-(2-methylphenyl)benzamide

Stage A: 4-[(5,8-Dibromo-2-naphthalenyl)methyl Benzoic Acid Chloride 3 drops of DMF (N,N-dimethylformamide) were added to a solution containing 0.90 g of 4-[(5,8-dibromo-2-naphthalenyl)methyl benzoic acid in 10 ml of methylene chloride. Then 0.22 ml of oxalyl chloride was added. Agitation was carried out for 2 hours at ambient temperature followed by concentrating. The product obtained was taken up in 6 ml of methylene chloride. In this way a solution of the acid chloride was obtained which was used as it was in the following stage.

Stage B: 4-[(5,8-Dibromo-2-naphthalenyl)methyl]-N-(2-methylphenyl)benzamide 0.20 ml of 2-methylphenylamine was introduced into 5 ml of methylene chloride. 0.26 ml of triethylamine was added. 3 ml of the solution of the acid chloride obtained in Stage A was added dropwise. The reaction medium was left under agitation for 4 hours at ambient temperature. The reaction mixture was poured into a normal solution of hydrochloric acid followed by extraction with methylene chloride, washing with a normal solution of hydrochloric acid, with a 0.5 N solution of soda, with a saturated ammonium chloride solution, filtering and concentrating. The product obtained was recrystallized from isopropyl ether followed by filtering and washing with diisopropyl ether then with pentane. The product obtained was dried under reduced pressure at 40° C. In this way 0.42 g of sought product was obtained.

EXAMPLE 3

4-[(5,6-Dichloro-1-fluoro-1,2,3,4-tetrahydro-2-naphthalenyl)methyl]-N-(2-methylphenyl)benzamide A solution containing 0.35 g of 4-[(5,6-dichloro-1-hydroxy-1,2,3,4-tetrahydro-2-naphthalenyl)methyl]-N-(2-methylphenyl)benzamide and 10 cm³ of methylene chloride is cooled down to −65°C.±5° C. 142 mg of DAST (diethylaminosulfur trifluoride) was added. The solution was maintained under agitation for 1 hour at −65° C. The temperature was allowed to rise to 20° C. and the reaction medium was poured into an aqueous solution of potassium acid carbonate, followed by agitation for 30 minutes and extraction with methylene chloride. The organic phases were collected, dried, filtered and concentrated. In this way 340 mg of sought product was obtained.

EXAMPLE 4

4[(5,8-Dibromo-2-naphthalenyl)fluoromethyl]-N-(2-methylphenyl)benzamide 0.27 g of 4-[(5,8-dibromo-2-naphthalenyl)hydroxymethyl]-N-(2-methylphenyl)benzamide was introduced into 25 ml of methylene chloride. The reaction medium was cooled down to −15° C. 0.1 ml of DAST was added dropwise and the reaction mixture was maintained under agitation for 4 hours. A product was obtained which was poured into a saturated solution of sodium bicarbonate, agitation was carried out at ambient temperature for 45 minutes followed by extraction with methylene chloride. The organic phases were collected, followed by washing with a saturated solution of sodium chloride, drying, filtering and evaporating to dryness. 0.3 g of product was obtained which was crystallized from a pentane/ethyl acetate mixture 7-3. After filtering and washing with a pentane/ethyl acetate mixture 9-1, then with pentane, 0.21 g of sought product was obtained.

Preparation 1: Methyl 4-[(3,4-Dihydro-6-methoxy-1-oxo-2 (1H)-naphthalenylidene)methyl]benzoate 5 g of 3,4-dihydro-6-methoxy-2(1H)-naphthalenone was dissolved in 80 ml of methanol. 4.65 g of methyl 3-formyl benzoate was added. 0.32 g of soda was added to the solution obtained, which was agitated for 66 hours at ambient temperature followed by separating, washing with methanol then with pentane and drying at 40° C. for 18 hours. In this way 6.36 g of sought product was obtained. M.p.=156° C.

Preparation 2: Methyl 4-[(7-Bromo-1,2,3,4-tetrahydronaphthalenyl)methyl]benzoate 1 g of methyl 4-[(7-bromo-3,4-dihydro-1-oxo-2(1H)-naphthalenyliden)methyl]benzoate was dissolved at 20° C. in 10 cm³ of chloroform. 4 cm³ of trifluoroacetic acid and 3 cm³ of triethylsilane were added. The reaction mixture was taken to reflux for 3 hours and 3 cm3 of Et₃SiH then 3 cm³ of trifluoroacetic acid were added.

The reaction medium was heated for 5 hours under reflux and maintained under agitation at 20° C. for 48 hours. The reaction mixture was poured into a mixture of water and ice and adjusted to a basic pH by the addition of sodium acid carbonate followed by extraction with methylene chloride, drying over magnesium sulfate and filtering then concentrating under reduced pressure at 40° C. The product obtained was chromatographed eluting with a heptane/ethyl acetate mixture 9-1. 488 mg of sought product was obtained. rf=0.3.

154 mg of methyl 4-[(7-bromo-3,4-dihydro-2-naphthalenyl)methyl]benzoate rf=0.25, and 210 mg of methyl 4-[(7-bromo-3,4-dihydro-1-oxo-2(1H)-naphthalenyl)]benzoate rf=0.1.

Preparation 3: Methyl 4-[8-Bromo-2-naphthalenyl)methyl]benzoate

A mixture of 537 mg of methyl 4-[(8-bromo-3,4-dihydro-2-naphthalenyl)methyl]benzoate and 48 mg of sulfur were agitated at ambient temperature while purging with nitrogen. The vessel containing the reaction mixture was immersed in a bath at 220° C. for 15 minutes. The product obtained was purified by chromatography eluting with a heptane-methyl terbutylate mixture 95-5. 266 mg of sought product was isolated.

Preparation 4: Methyl 4-[(1-Hydroxy-1,2,3,4-tetrahydro-6-methoxy-2-naphthalenyl)methyl]benzoate 4 g of methyl 4-[(1,2,3,4-tetrahydro-6-methoxy-1-oxo-2-naphthalenyl)methyl]benzoate and 100 ml of anhydrous methanol were mixed together and 100 ml of THF (tetrahydrofuran) was added. 0.47 g of sodium borohydride was added and the reaction medium was agitated for 2 hours 30 minutes at ambient temperature, another 0.47 g of sodium borohydride was added and agitation was continued for 30 minutes at 20° C. The reaction medium was treated with a solution of sodium acid phosphate, followed by agitation for 5 minutes, saturation with sodium chloride and extraction with ethyl acetate. After drying and concentrating the product obtained was washed and dried. In this way 3.9 g of sought product was obtained melting at 112° C.

Preparation 5: Methyl 4-[(1,2,3,4-Tetrahydro-6-methoxy-1-oxo-2-naphthalenyl)methyl]benzoate 750 mg of 10% palladium on carbon was added to a solution containing 7.39 g of methyl 4-[(3,4-dihydro-6-methoxy-1-oxo-2(1H)-naphthalenylidene)methyl]benzoate and 200 ml of THF. The reaction medium was purged with nitrogen, with hydrogen and agitated under 1 bar of hydrogen pressure. After agitation for 2 hours the reaction medium was filtered and concentrated. 8 g of product was obtained which was purified on silica eluting with a heptane/dioxan mixture 8-2. In this way 4.92 g of sought product was isolated melting at 121° C.

Preparation 6: Methyl 4-[(3,4-Dihydro-6-methoxy-2-naphthalenyl)methyl]benzoate 150 mg of PTSA (p-toluene sulfonic acid) was added to a mixture containing 1.5 g of methyl 4-[(1-hydroxy-1,2,3,4-tetrahydro-6-methoxy-2-naphthalenyl)methyl]benzoate and 40 ml of toluene. The reaction medium was taken to reflux for 30 minutes, cooled down to ambient temperature, washed with a solution of sodium acid carbonate, dried and concentrated. A product was obtained which was purified by eluting with a heptane/dioxan mixture 8-2. In this way 1.35 g of sought product was isolated rf=0.25.

Preparation 7: Methyl 4-[(8-Bromo-3,4-dihydro-2-naphthalenyl)methyl]benzoate 1.77 g of potassium terbutylate was added at 20° C. to a suspension containing 7.37 g of [[4-(methoxycarbonyl)phenyl]methyl]triphenyl-phosphonium bromide and 60 ml of anhydrous toluene. Agitation was carried out for 45 minutes and 2.25 g of 8-bromo-3,4-dihydro-2-(1H)-naphthalenone dissolved in 12 ml of toluene was added. The reaction medium was heated to 75~80° C. for 4 hours and 30 minutes, and then maintained at 20° C. for 18 hours. A dilute solution of sodium acid phosphate was added and extraction was carried out with toluene. The organic phases were dried over magnesium sulfate, concentrated and 10 g of product was obtained which is chromatographed on silica eluting with a heptane/isopropyl ether mixture 8-2. In this way 1.85 g of sought product was obtained.

Preparation 8A: Methyl 4-[(6-Chloro-1,2,3,4-tetrahydro-2-naphthalenyl)methyl]benzoate A mixture of 0.4 g of methyl 4-[(6-chloro-3,4-dihydro-2-naphthalenyl)methyl]benzoate, a catalytic quantity of 10% palladium on carbon and 10 ml of ethyl acetate was agitated at 25° C. for 2 hours under atmospheric pressure of hydrogen, followed by separating, rinsing and bringing to dryness under reduced pressure. 0.4 g of sought product was obtained. rf=0.5 heptane/ethyl acetate 7-3. rf=0.5.

Preparation 8B: Methyl 4-[(6-Chloro-3,4-dihydro-2-naphthalenyl)methyl]benzoate 65 mg of sodium hydride at 50% in oil was added to a solution containing 240 mg of methyl 4-[(6-chloro-3,4-dihydro-2-naphthalenyl)methyl]benzoate and methyl 4-[(6-chloro-1,2,3,4-tetrahydro-2-naphthalenylidene)methyl]benzoate and 20 ml of methanol. The reaction medium was heated under reflux for 4 hours, cooled down and poured into a dilute solution of sodium acid phosphate. Extraction was carried out with methylene chloride followed by drying over magnesium sulfate and concentration. 240 mg of sought product was obtained.

Preparation 9: 1,1-Dimethylethyl 4-[(5,8-Dibromo-2-naphthalenyl)hydroxymethyl]benzoate 5,8 g of 1,1-dimethylethyl 4-iodo benzoate was introduced into 120 ml of THF. 50 mg of o-phenanthroline was added followed by cooling down to a temperature of −95/−100° C. 16 ml of a 1.6 M solution of n-butyllithium in hexane was added dropwise, then the reaction medium is maintained under agitation at −100° C. for 5 minutes and a solution of 5 g of 5,8-dibromo-2-naphthalene carboxaldehyde in 20 ml of THF was added. The temperature was allowed to return to ambient and the whole was poured into a saturated solution of potassium acid phosphate, followed by extraction with ethyl ether. The ethereal phases were collected, washed with a saturated solution of sodium chloride, dried, filtered and concentrated. 11 g of a product was obtained which was purified by chromatography on silica eluting with a heptane/diisopropyl ether mixture (65-35). In this way the sought product was obtained rf=0.15.

Preparation 10: 4-[(5,8-Dibromo-2-naphthalenyl)methyl]benzoic Acid 3.85 g of 1,1-dimethylethyl (5,8-dibromo-2-naphthalenyl)hydroxymethyl]benzoate was added to a mixture of 80 ml of acetonitrile and 80 ml of acetone. The reaction medium was cooled down to 5° C. and 9.5 g of sodium iodide was added. 3.85 ml of dimethylsilyl chloride was added dropwise followed by agitation overnight at ambient temperature. The reaction medium was poured over ice, extracted with methylene chloride and ethyl ether. The organic phases were collected, washed with 1% sodium thiosulfate, with water, then with a saturated solution of sodium chloride, followed by drying, filtering and concentrating. 6.3 g of a product was obtained which was chromatographed on silica eluting with a heptane/ethyl acetate mixture 7-3 with 1% acetic acid. The sought product was obtained. rf=0.15.

Preparation 11: 4-[(5,8-Dibromo-2-naphthalenyl)acetyloxymethyl]benzoic Acid 1.5 ml of pyridine and 1 ml of acetic anhydride were added to a solution containing 1.55 g of 1,1-dimethylethyl 4-[(5,8-dibromo-2-naphthalenyl)hydroxymethyl]benzoate and 15 ml of methylene chloride. The reaction medium was maintained under agitation at ambient temperature for 2 hours. The product obtained was chromatographed on silica eluting with a heptane/diisopropyl ether mixture 6-4. The product obtained was poured into a saturated solution of potassium acid phosphate followed by extraction with methylene chloride. The organic phases were collected, washed with a 1N solution of hydrochloric acid, then with a saturated solution of sodium chloride, dried, filtered and concentrated. 2 g of a product was obtained which was chromatographed on silica eluting with a heptane/diisopropyl ether mixture 6-4. After evaporation of the fractions with an rf=0.25, the product was obtained which was recrystallized from pentane. Filtering was carried out followed by washing and drying in a dessicator at 35° C. under reduced pressure and 1.22 g of sought product was obtained.

Preparation 12: 5,6-Dibromo-3,4-dihydro-2(1H)-naphthalenone 4.4 ml of oxalyl chloride and a few drops of DMF were added at 0° C. to a solution containing 11 g of 5,6-dibromophenylacetic acid and 100 ml of methylene chloride. The reaction medium was agitated overnight at ambient temperature and brought to dryness under reduced pressure. The product obtained was introduced into 50 ml of methylene chloride then this solution was introduced dropwise at −20° C. into a mixture of 10 g of aluminum chloride and 40 ml of methylene chloride. A suspension was obtained which was kept at −20° C. A stream of ethylene was passed through it for 1 hour and 15 minutes. The reaction medium was poured over ice, extracted with methylene chloride, washed with an aqueous solution of sodium bicarbonate, dried and brought to dryness. The product obtained was chromatographed on silica eluting with a heptane/ethyl acetate mixture 70-30. The isomers obtained were separated by successive crystallizations from an isopropyl ether/methylene chloride system. In this way 30% of 5,6-dibromo-3,4-dihydro-2(1H)-naphthalenone compound was obtained, and 20% of 7,8 dibromo-3,4-dihydro-2(1H)-naphthalenone isomer was obtained.

By using the processes described above the following products were prepared:

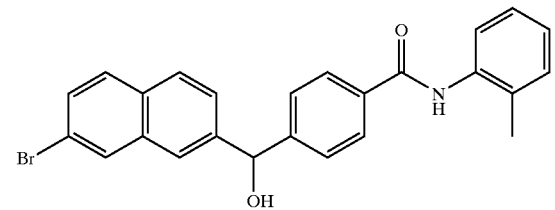

M.P. = 200° C.

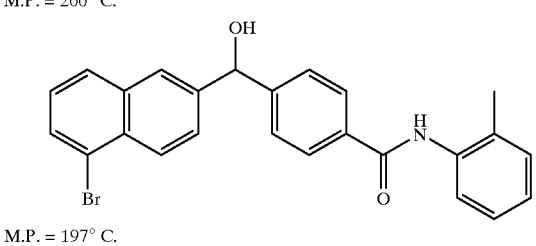

M.P. = 197° C.

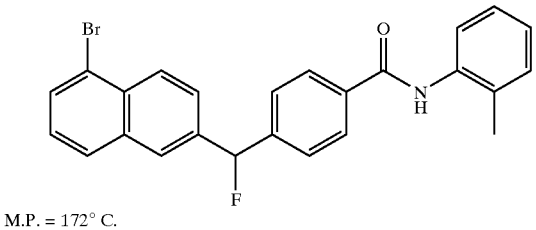

M.P. = 172° C.

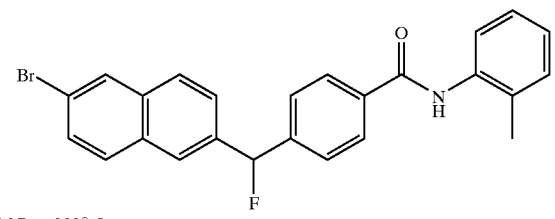

M.P. = 203° C.

-continued
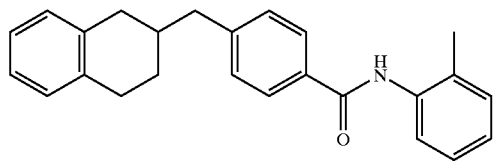
M.P. = 149° C.
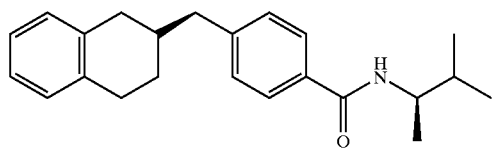
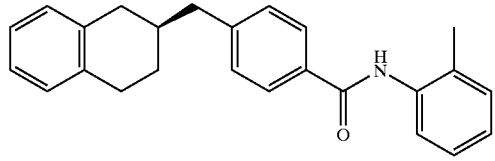
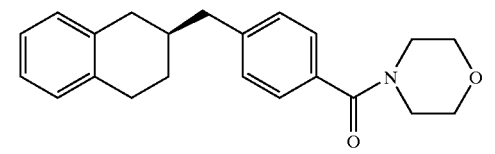
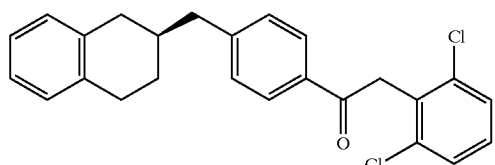
M.P. = 127° C.
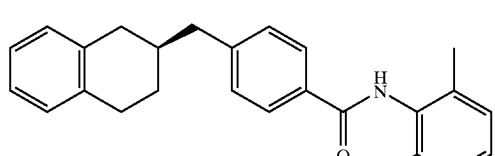
M.P. = 150° C.
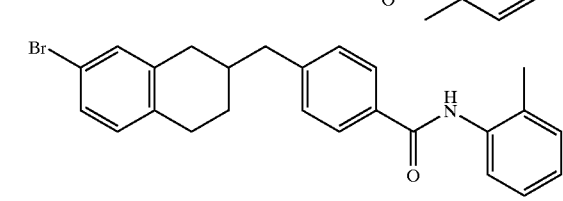
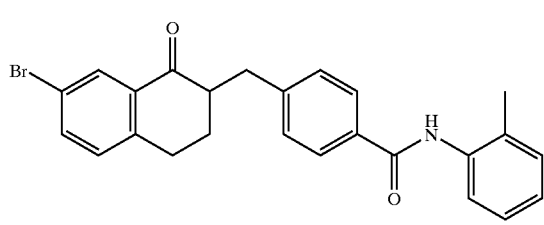
M.P. = 137° C.
M.P. = 178° C.
-continued
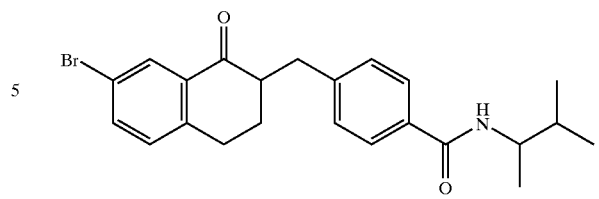
M.P. = 154° C.
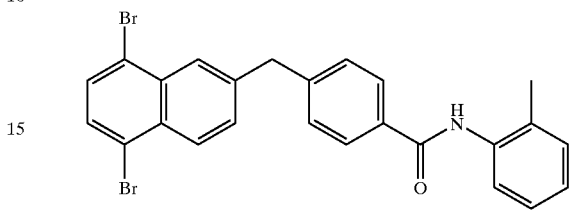
M.P. = 202° C.
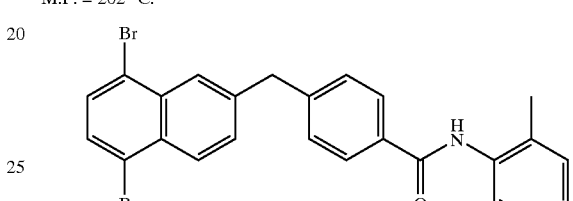
M.P. = 199° C.
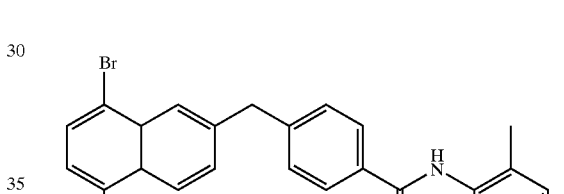
M.P. = 187° C.
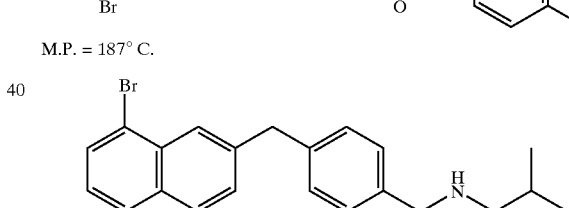
M.P. = 163° C.
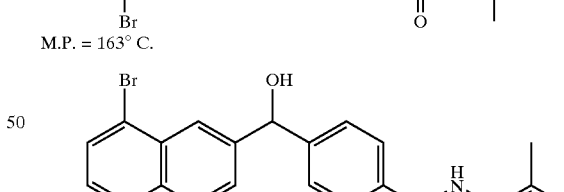
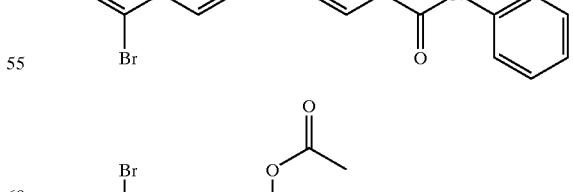
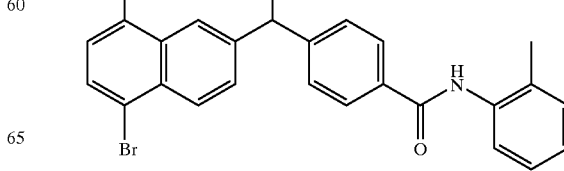

-continued
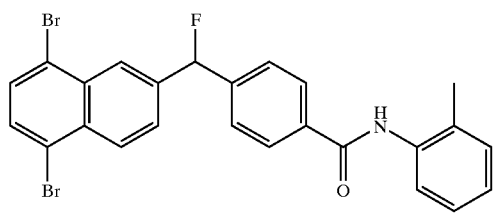
M.P. = 216° C.
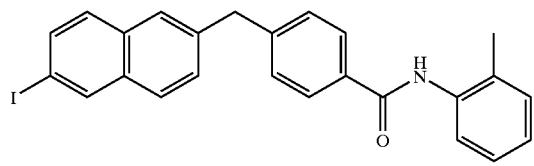
M.P. = 174° C.
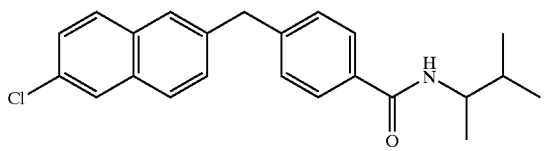
M.P. = 167° C.
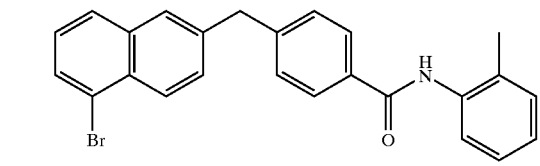
M.P. = 170° C.
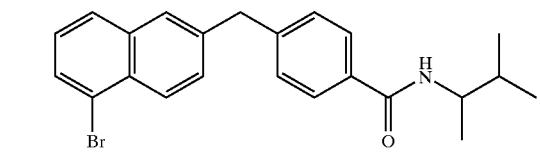
M.P. = 170° C.
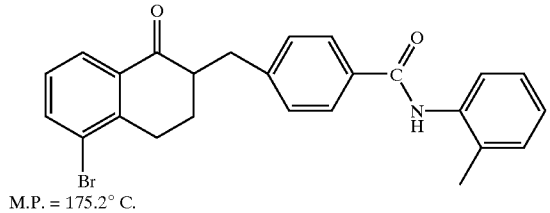
M.P. = 175.2° C.
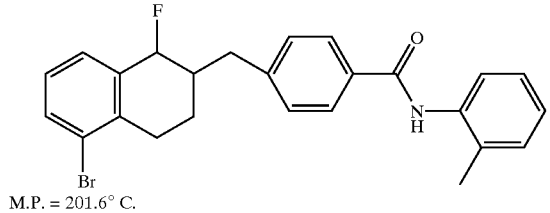
M.P. = 201.6° C.
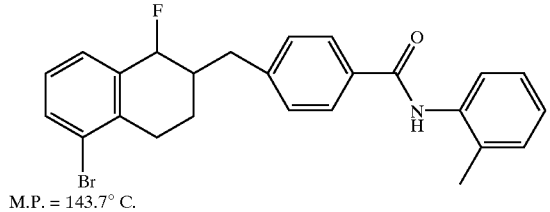
M.P. = 143.7° C.
-continued
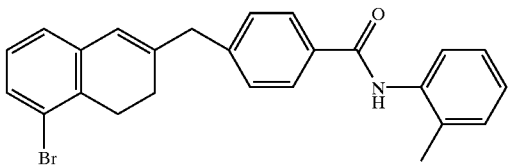
M.P. = 168.7° C.
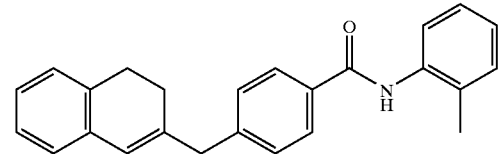
M.P. = 132° C.
M.P. = 179° C.
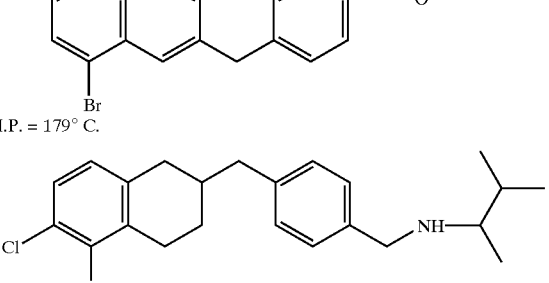
M.P. = 172.4° C.
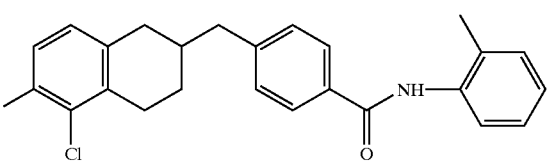
M.P. = 178.9° C.
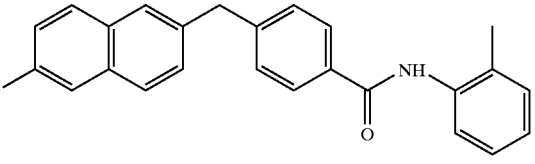
M.P. = 180.6° C.
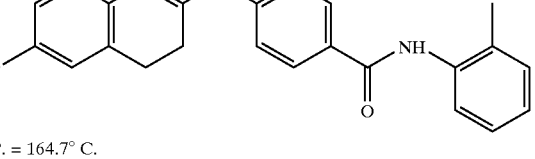
M.P. = 164.7° C.
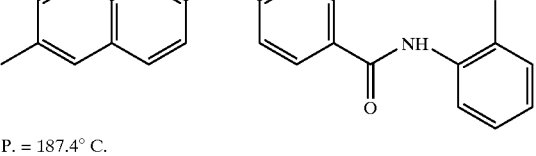
M.P. = 187.4° C.

-continued
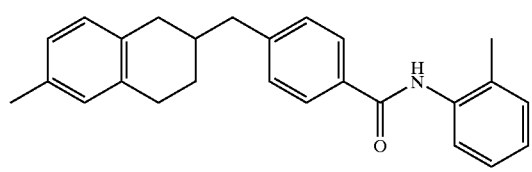
M.P. = 153.5° C.
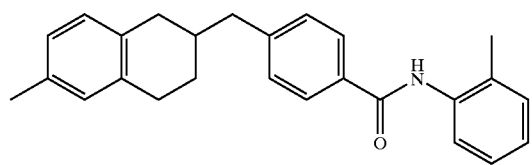
M.P. = 154° C.
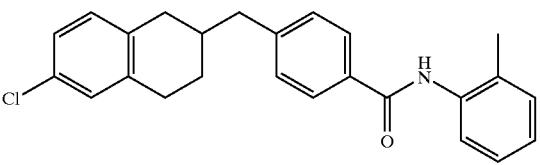
M.P. = 139.4° C.
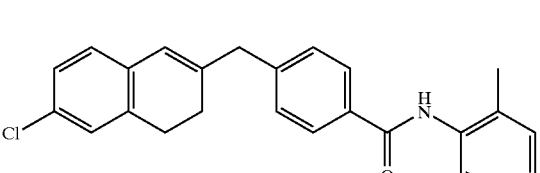
M.P. = 162° C.
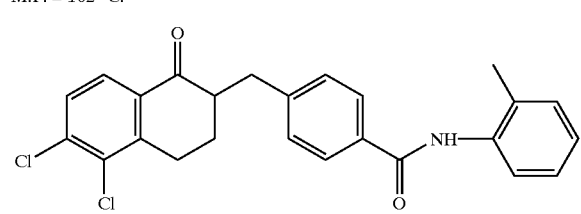
M.P. = 177° C.
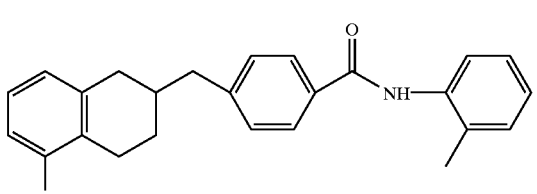
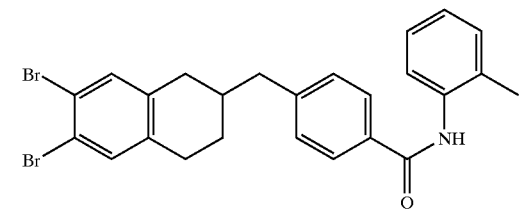
M.P. = 172° C.
-continued
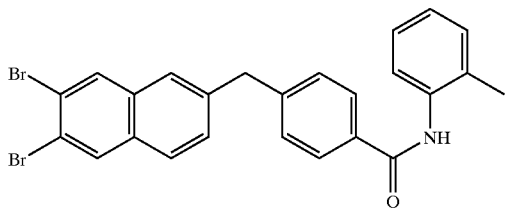
M.P. = 184° C.
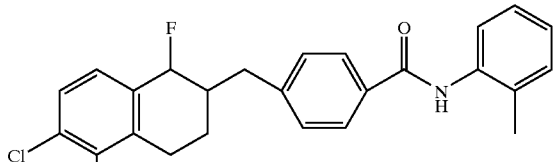
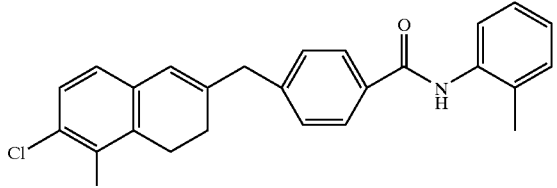
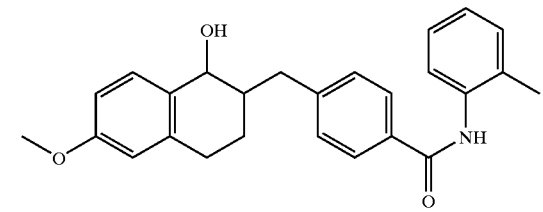
M.P. = 145° C.
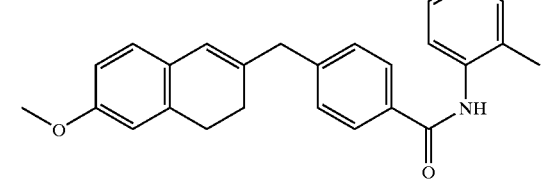
M.P. = 162° C.
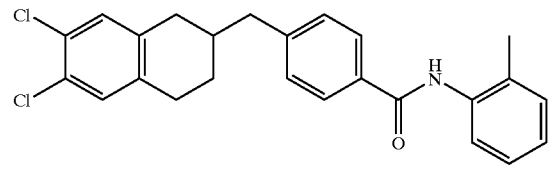
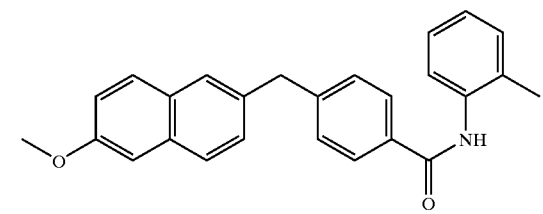
M.P. = 167° C.

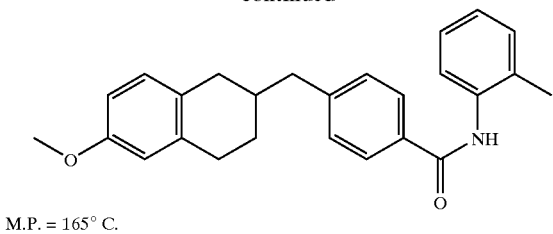

M.P. = 165° C.

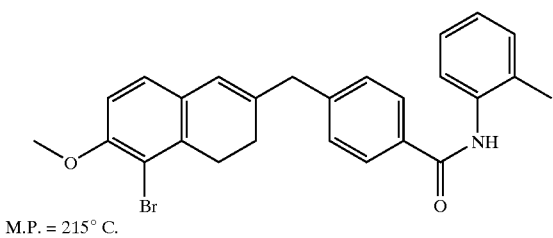

M.P. = 215° C.

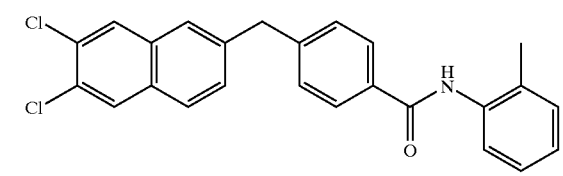

M.P. = 177° C.

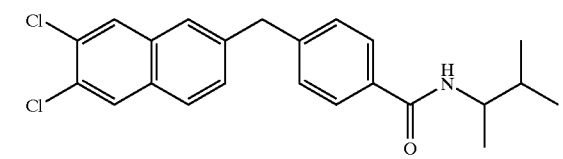

M.P. = 183° C.

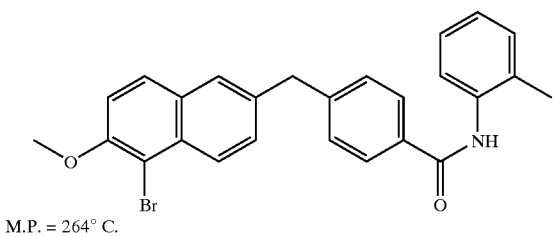

M.P. = 264° C.

Among the products of the invention, there can in particular be mentioned the following products, which were prepared as follows:

Product A:

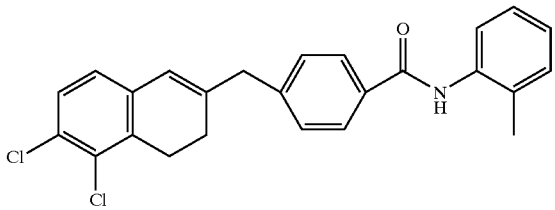

rf=0.26
Heptane/ethyl acetate 7-3

| Starting material: | Operating method: |
|---|---|
| 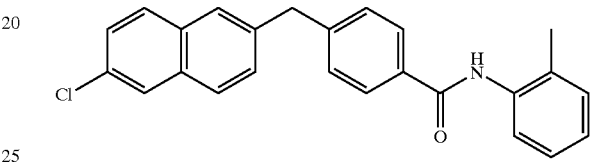 | Prep. 1<br>Prep. 2 |

Product B:

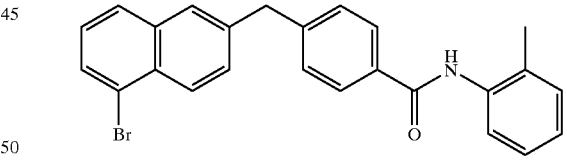

rf=0.38
CH$_2$Cl$_2$—AcOEt 98/2

| Starting material: | Operating method: |
|---|---|
| ![naphthalene-CHO with Br] | Prep.<br>Prep. 10<br>Ex. 2 |

Product C:

![Product C structure]

rf=0.33
CH$_2$Cl$_2$—AcOEt 98/2

| Starting material: | Operating method: |
|---|---|
| ![naphthalene-CHO with Br] | Prep. 9<br>Prep. 10<br>Ex. 2 |

Product D:

M.p.=180.6° C.

| Starting material: | Operating method: |
|---|---|
| 4-bromophenylacetic acid (Commercial product) | Prep. 12<br>Prep. 7<br>Prep. 3<br>Ex. 1 |

Product E:

M.p.=164.7° C.

| Starting material: | Operating method: |
|---|---|
| 4-bromophenylacetic acid (Commercial product) | Prep. 12<br>Prep. 7<br>Ex. 1 |

Product F:

M.p.=139.4° C.

| Starting material: | Operating method: |
|---|---|
| 4-chlorophenylacetic acid | Prep. 12<br>Prep. 7<br>Prep. 8<br>Ex. 1 |

Product G:

M.p.=162° C.

| Starting material: | Operating method: |
|---|---|
| 4-chlorophenylacetic acid | Prep. 12<br>Prep. 7<br>Ex. 1 |

Product H:

M.p.=172° C.

| Starting material: | Operating method: |
|---|---|
| 6,7-dibromo-2-tetralone | Prep. 12<br>Prep. 7<br>Ex. 1 |

Product I:

M.p.=184° C.

| Starting material: | Operating method: |
|---|---|
| 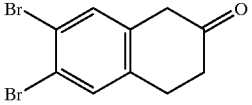 | Prep. 12<br>Prep. 7<br>Prep. 3<br>Ex. 1 |

Product J:

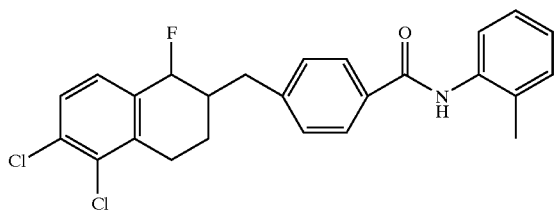

rf=0.27
Heptane/ethyl acetate 7-3

| Starting material: | Operating method: |
|---|---|
| 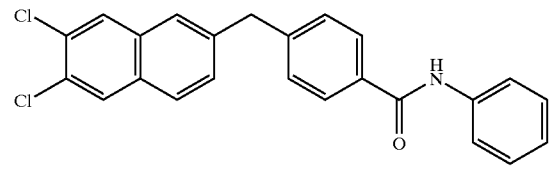 | Prep. 1<br>Prep. 2<br>Prep. 4<br>Ex. 1 |

Product K:

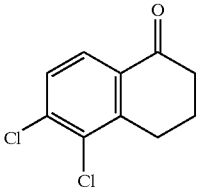

M.p.=177° C.

| Starting material: | Operating method: |
|---|---|
| 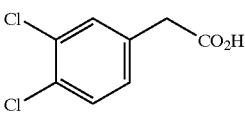 | Prep. 12<br>Prep. 7<br>Prep. 3<br>Ex. 1 |

Product L:

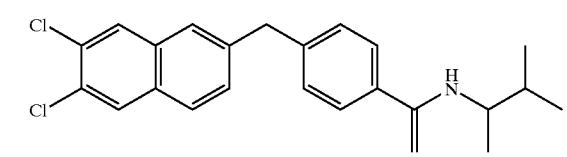

rf=0.20
CH$_2$Cl$_2$—AcOEt 98/2

| Starting material: | Operating method: |
|---|---|
| Cl-C6H4-CHO | Prep. 9<br>Prep. 10<br>Ex. 2 |

Product M:

M.p.=183° C.

| Starting material: | Operating method: |
|---|---|
| 3,4-Cl2-C6H3-CH2-CO2H | Prep. 12<br>Prep. 7<br>Prep. 3<br>Ex. 1 |

Preparation of Compositions

In the examples of compositions below, the following signs signify:

* Surfactant
Reacts by forming the polyurea walls of the microcapsule.

| 1. Emulsifiable concentrate. | |
|---|---|
| Active ingredient | 10.00 |
| Ethoxylated alkylphenol* | 7.50 |
| Alkylarylsulfonate* | 2.50 |
| C8-C13 aromatic solvent | 80.00 |
| | 100.00 |
| 2. Emulsifiable concentrate. | |
| Active ingredient | 10.00 |
| Ethoxylated alkylphenol* | 2.50 |
| Alkylarylsulfonate* | 2.50 |
| Ketonic solvent | 64.00 |
| C8-13 aromatic solvent | 18.00 |
| Antioxidant | 3.00 |
| | 100.00 |

3. Wettable powder.

| | |
|---|---|
| Active ingredient | 5.00 |
| C8-13 aromatic solvent | 7.00 |
| C18 aromatic solvent | 28.00 |
| Kaolin | 10.00 |
| Alkylarylsulfonate* | 1.00 |
| Naphthalenesulfonic acid* | 3.00 |
| Diatomaceous earth | 46.00 |
| | 100.00 |

4. Dusting powder.

| | |
|---|---|
| Active ingredient | 0.50 |
| Talc | 99.50 |
| | 100.00 |

5. Bait.

| | |
|---|---|
| Active ingredient | 0.5 |
| Sugar | 79.5 |
| Paraffin wax | 20.0 |
| | 100.00 |

6. Concentrate in emulsion.

| | |
|---|---|
| Active ingredient | 5.00 |
| C8-13 aromatic solvent | 32.00 |
| Cetyl alcohol | 3.00 |
| Polyoxyethyleneglycerol monooleate* | 0.75 |
| Polyoxyethylenesorbitan esters* | 0.25 |
| Silicon solution | 0.10 |
| Water | 58.90 |
| | 100.00 |

7. Concentrate in suspension.

| | |
|---|---|
| Active ingredient | 10.00 |
| Ethoxylated alkoylphenol* | 3.00 |
| Silicon solution | 0.10 |
| Alkanediol | 5.00 |
| Fumed silica | 0.50 |
| Xanthane gum | 0.20 |
| Water | 80.00 |
| Buffer | 1.20 |
| | 100.00 |

8. Microemulsion.

| | |
|---|---|
| Active ingredient | 10.00 |
| Polyoxyethleneglycerol monooleate* | 10.00 |
| Alkanediol | 4.00 |
| Water | 76.00 |
| | 100.00 |

9. Granules dispersible in water.

| | |
|---|---|
| Active ingredient | 70.00 |
| Polyvinylpyrrolidine | 2.50 |
| Ethoxylated alkylphenol | 1.25 |
| Alkylarylsulfonate | 1.25 |
| Kaolin | 25.00 |
| | 100.00 |

10. Granules.

| | |
|---|---|
| Active ingredient | 2.00 |
| Ethoxylated alkylphenol* | 5.00 |
| Alkylarylsulfonate* | 3.00 |
| C8-13 aromatic solvent | 20.00 |
| Kieselguhr granules | 70.00 |
| | 100.00 |

11. Aerosol (aerosol can).

| | |
|---|---|
| Active ingredient | 0.30 |
| Piperonylbutoxide | 1.50 |
| C8-13 saturated hydrocarbonated solvent | 10.0 |
| Sorbitan monooleate* | 1.0 |
| Water | 40.0 |
| Butane | 48.7 |
| | 100.00 |

12. Aerosol (aerosol can).

| | |
|---|---|
| Active ingredient | 0.3 |
| C8-13 saturated hydrocarbonated solvent | 10.0 |
| Sorbitan monooleate* | 1.0 |
| Water | 40.0 |
| Butane | 48.7 |
| | 100.00 |

13. Aerosol (aerosol can).

| | |
|---|---|
| Active ingredient | 1.00 |
| CO2 | 3.00 |
| Polyoxyethleneglycerol monooleate* | 1.40 |
| Propane | 38.00 |
| Water | 56.60 |
| | 100.00 |

14. Lacquer.

| | |
|---|---|
| Active ingredient | 2.50 |
| Resin | 5.00 |
| Antioxidant | 0.50 |
| Very aromatic white spirit | 92.00 |
| | 100.00 |

15. Spray (ready to use).

| | |
|---|---|
| Active ingredient | 0.10 |
| Antioxidant | 0.10 |
| Odorless kerosene | 99.80 |
| | 100.00 |

16. Potentiated spray (ready to use).

| | |
|---|---|
| Active ingredient | 0.10 |
| Piperonylbutoxide | 0.50 |
| Antioxidant | 0.10 |
| Odorless kerosene | 99.30 |
| | 100.00 |

17. Microcapsules.

| | |
|---|---|
| Active ingredient | 10.0 |
| C8-13 aromatic solvent | 10.0 |
| Aromatic diisocyanate # | 4.5 |
| Ethoxylated alkylphenol* | 6.0 |
| Alkyldiamine # | 1.0 |
| Diethylenetriamine | 1.0 |
| Concentrated hydrochloric acid | 2.2 |
| Xanthane gum | 0.2 |
| Fumed silica | 0.5 |
| Water | 64.6 |
| | 100.00 |

18. Dispersable concentrate.

| | |
|---|---|
| Active ingredient | 5.00 |
| N-methylpyrrolidinone | 15.00 |
| N-alkylpyrrolidinone | 53.00 |
| C8-13 aromatic solvent | 16.00 |
| Nonylphenol polyoxyethylenic ether phosphate | 6.00 |
| Ethoxylated alkylphenol | 3.50 |
| Alkylarylsulfonate | 1.30 |
| Polyalkyleneglycolic ether | 0.20 |
| | 100.00 |

19. Soluble concentrate.

A homogenous mixture is prepared of:

| | |
|---|---|
| Active ingredient | 0.25 |
| Piperonyl butoxide | 1.00 |
| Tween 80 | 0.25 |
| Topanol A | 0.10 |
| Water | 98.40 |
| | 100.00 |

20. Emulsifiable concentrate.

A homogenous mixture is prepared of:

| | |
|---|---|
| Active ingredient | 0.0015 |
| Piperonyl butoxide | 0.50 |
| Topanol A | 0.10 |
| Tween 80 | 3.5 |
| Xylene | 95.885 |
| | 100.00 |

Study of the Biological Activity

A) Study on Phaedon Cochleariae

The product was dissolved at the desired concentration in an acetone-water mixture (50-50). Foliar disks of Chinese cabbage (*Brassica pekinensis*) were immersed for five seconds in the solution, then left to dry for one hour. Ten adults (a mixture of males and females) were added into a Petri dish containing a foliar disk. These were kept at a temperature of 25° C., with a photoperiod of twelve hours. After seven days, the mortality of the insects was checked and the foliar surface consumed is evaluated.

Product A had a very useful activity on this batch at a dose of 300 ppm.

B) Study on Spodoptera Littoralis

The product was dissolved at the desired concentration in an acetone-water mixture (50-50). Haricot leaves (*Phaseolus vulgaris*, var. Delinel) were immersed for five seconds in the solution, then left to dry in a Petri dish for one hour. Ten larvae of Spodoptera littoralis were then added to each dish. These are were at a temperature of 25° C., with a photoperiod of twelve hours. After seven days, the mortality of the larvae was checked and the foliar surface consumed is evaluated.

Products A, B, C, D, E, F, G, H, I, J, K had a very good activity starting from a dose of 300 ppm.

C) Study on Heliothis Virescens

The product was dissolved at the desired concentration in an acetone-water mixture (50-50). 50 µl of solution is deposited on the surface of small well containing approximately 2 grams of plant based artificial medium. One neonate larva of *Heliothis virescens* was then introduced into each well, which was sealed with a sheet of cellophane. The tests were kept at a temperature of 25° C., with a photoperiod of twelve hours., The mortality of the larvae was checked after seven days.

Products A, B, C, D, E, F, G, H, I, J, K, L and M had a very good activity starting from a dose of 300 ppm.

D) Study of the Activity on Diabrotica

The test insects were final stage larvae of *Diabrotica undecimpunctata*.

A 9 cm disc of filter paper, placed at the bottom of Petri dish, was treated using 1 cm³ of an acetone solution. After drying 15 larvae per dose were deposited and the mortality check was carried out 24 hours after treatment.

Products A, L and M had a very good activity starting from a dose of 300 ppm.

What is claimed is:

1. A compound of the formula

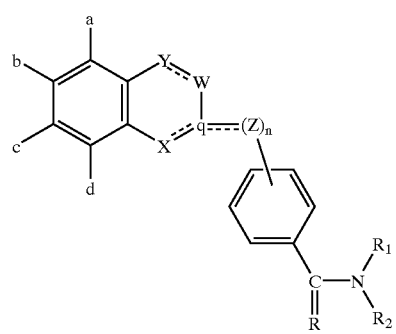

in which a, b, c and d, identical to or different from one another, represent a hydrogen atom, a halogen atom, an alkyl, alkenyl or alkynyl, O-alkyl, O-alkenyl or O-alkynyl, S-alkyl, S-alkenyl or S-alkynyl radical containing up to 8 carbon atoms, optionally substituted by one ore more halogen atoms, a C≡N, $NO_2$ or $NH_2$ radical, the substituents a, b, c, and d being able to form between themselves rings, which either contain or do not contain one or more hetero atoms, and which are substituted or unsubstituted, wherein i) when Y and W, identically or different, represent

where e' is a hydrogen atom, a halogen atom, a free, etherified or esterified hydroxyl radical, or an optionally halogen substituted $C_1$–$C_8$ alkyl radical, X represents

where g and h identical or different represent a hydrogen atom, a halogen atom, a free etherified or esterified hydroxyl radical, or an alkyl radical containing up to 8 carbon atoms optionally substituted by one or more halogen atoms, or X represents a C═O radical, an oxygen atom or a nitrogen atom, or X forms with the carbon in 2-position belonging to radical q an epoxy bridge, a cyclic hydrocarbonated radical optionally substituted by one or more halogen atoms; and q is a C═ radical or a CD radical in which D represents a hydrogen atom, a halogen atom or an alkyl or alkoxy radical containing up to 8 carbon atoms optionally substituted by one or more halogen atoms, or D forms with the carbon atom which carries it and one of the carbon atoms adjacent to it a carbon-carbon double bond, an epoxy radical, a cyclic hydrocarbonated radical, optionally substituted by one or more halogen atoms;

ii) when Y and W identical of different represent

where e and f, identical or different, are a hydrogen atom, a halogen atom, a free, etherified or esterified hydroxyl radical, or an alkyl radical containing up to 8 carbon atoms optionally substituted by one or more halogen atoms;

X represents

where g' is identical or different is a hydrogen atom, a halogen atom, a free, etherified or esterified hydroxyl radical, or an alkyl radical containing up to 8 carbon atoms optionally substituted by one or more halogen atoms or X represents a C═O radical, an oxygen atom or a nitrogen atom, or X forms with the carbon in the 2-position belonging to radical q an epoxy bridge, a cyclic hydrocarbonated radical optionally substituted by one or more halogen atoms; and q represents a C= radical or a CD radical, in which D represents a hydrogen atom, a halogen atom or an alkyl or alkoxy radical containing up to 8 carbon atoms optionally substituted by one or more halogen atoms, or D forms with the carbon atom which carries it and one of the carbon atoms adjacent to it a carbon-carbon double bond, an epoxy radical, a cyclic hydrocarbonated radical, optionally substituted by one or more halogen atoms;

or iii) Y and W identical or different represent

where e and f, identical or different, are a hydrogen atom, a halogen atom, a free, etherified or esterified hydroxyl radical, or an alkyl radical containing up to 8 carbon atoms optionally substituted by one or more halogen atoms;

X represents

where g and h identically or different represent a hydrogen atom, a halogen atom, a free etherified or esterified hydroxyl radical, or an alkyl radical containing up to 8 carbon atoms optionally substituted by one or more halogen atoms, or X represents a C=O radical, an oxygen atom or a nitrogen atom, or X forms with the carbon in position 2 belonging to radical q an epoxy bridge, a cyclic hydrocarbonated radical optionally substituted by one or more halogen atom; and q represents a C= radical or a CD radical in which D represents a hydrogen atom, a halogen atom or an alkyl or alkoxy radical containing up to 8 carbon atoms optionally substituted by one or more halogen atoms, or D forms with the carbon atom which carries it and one of the carbon atoms adjacent to it a carbon-carbon double bond, an epoxy radical, a cyclic hydrocarbonated radical, optionally substituted by one or more halogen atoms;

n represents an integer varying from 0 to 8,

Z represents

in which l and k, identical or different, represent a hydrogen atom, a halogen atom, a C≡N radical, a free, etherified or esterified hydroxyl radical, an SR' radical wherein R' is an organic group containing up to 8 carbon atoms or an alkyl radical containing up to 8 carbon atoms optionally substituted by one or more halogen atoms, or Z represents an oxygen, sulfur, nitrogen atom, a C=O or C=S radical, it being understood that if n is greater than 1, Z can take different values, R represents an oxygen or sulfur atom;

$R_1$ and $R_2$, identical to or different from one another, represent a hydrogen atom, a linear, branched or cyclic, saturated or unsaturated, optionally substituted alkyl, CO-alkyl, CONH-alkyl or $CO_2$ alkyl radical, said alkyl radical, optionally interrupted by one or more heteroatoms and containing up to 8 carbon atoms, or an optionally substituted aryl or heteroaryl radical, the —C—$(Z)_n$ chain is fixed in position 3 or 4 of the benzamide, the dotted lines representing one or more optional double bonds, in all its possible isomeric forms as well as mixtures of said forms.

2. A compound of the formula

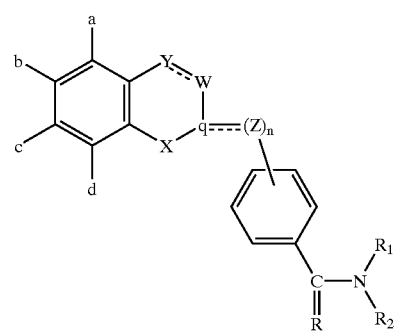

(I)

in which a, b, c, and d identical to or different from one another, represent a hydrogen atom, a halogen atom, an alkyl, alkenyl or alkynyl, O-alkyl, O-alkenyl or O-alkynyl, S-alkyl, S-alkenyl or S-alkynyl radical containing up to 8 carbon atoms, optionally substituted by one ore more halogen atoms, a C≡N, $NO_2$ or $NH_2$ radical, the substituents a, b, c, and d being able to form between themselves rings, which either contain or do not contain one or more hetero atoms, and which are substituted or unsubstituted;

Y and W, identical to or different from one another, both represent a radical of the formula

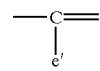

or both represent a radical of the formula

in which e, f, and e', identical or different, represent a hydrogen atom, a halogen atom, a free, etherified or esterified hydroxyl radical, or an alkyl radical containing up to 8 carbon atoms optionally substituted by one or more halogen atoms;

X represents a radical of the formula

or a radical of the formula

in which
g, h, and g', identical or different, represent a hydrogen atom, a halogen atom, a free, etherified or esterified hydroxyl radical, or an alkyl radical containing up to 8 carbon atoms optionally substituted by one or more halogen atoms, or X represents a C=O radical, an oxygen atom or a nitrogen atom, or X forms with the carbon in 2-position belonging to radical q an epoxy bridge, a cyclic hydrocarbonated radical optionally substituted by one or more halogen atoms;

q represents a C= radical or a CD radical, in which D represents a hydrogen atom, a halogen atom or an alkyl or alkoxy radical containing up to 8 carbon atoms optionally substituted by one or more halogen atoms, or D forms with carbon atom which carries it and one of the carbon atoms adjacent to it a carbon-carbon double bond, an epoxy radical, a cyclic hydrocarbonated radical, optionally substituted by one or more halogen atoms;

n represents an integer varying from 0 to 8,

Z represents

in which
l and k, identical
or different, represent a hydrogen atom, a halogen atom, a C≡N radical, a free, etherified or esterified hydroxyl radical, an SR' radical wherein R' is an organic group containing up to 8 carbon atoms or an alkyl radical containing up to 8 carbon atoms optionally substituted by one or more halogen atoms, or Z represents an oxygen, sulfur, nitrogen atom, a C=O or C=S radical, it being understood that if n is greater than 1, Z can take different values, R represents an oxygen or sulfur atom;

$R_1$ and $R_2$, identical to or different from one another, represent a hydrogen atom, a linear, branched or cyclic, saturated or unsaturated, optionally substituted alkyl, CO-alkyl, CONH-alkyl or $CO_2$-alkyl radical, said alkyl radical, where said alkyl radical is optionally interrupted by one or more heteroatoms and contains up to 8 carbon atoms, or an optionally substituted aryl or heteroaryl radical, the —C—$(Z)_n$ chain is fixed in position 3 or 4 of the benzamide, the dotted lines representing one or more optional double bonds, in all its possible isomeric forms as well as its mixtures wherein at least one of the substituents a, b, c, or d represents a halogen atom.

3. A pesticidal composition for combating harmful arthropods and/or helminthes which comprises at least one compound of the formula

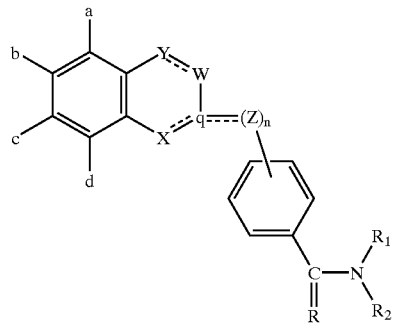

in which
a, b, c, and d, identical to or different from one another, represent a hydrogen atom, a halogen atom, an alkyl, alkenyl or alkynyl, O-alkyl, O-alkenyl or O-alkynyl, S-alkyl, S-alkenyl or S-alkynyl radical containing up to 8 carbon atoms, optionally substituted by one or more halogen atoms, a C≡N, $NO_2$ or $NH_2$ radical, the substituents a, b, c, and d being able to form between themselves rings, which either contain or do not contain one or more hetero atoms, and which are substituted or unsubstituted;

wherein
i) when Y and W, identically or different, represent

where
e' is a hydrogen atom, a halogen atom, a free, etherified or esterified hydroxyl radical, or an optionally halogen substituted $C_1$–$C_8$ alkyl radical, X represents

where
g and h identical or different represent a hydrogen atom, a halogen atom, a free etherified or esterified hydroxyl radical, or an alkyl radical containing up to 8 carbon atoms optionally substituted by one or more halogen atoms, or X represents a C=O radical, an oxygen atom or a nitrogen atom, or X forms with the carbon in 2-position belonging to radical q an epoxy bridge, a cyclic hydrocarbonated radical optionally substituted by one or more halogen atoms; and q is a C= radical or a CD radical in which D represents a hydrogen atom, a halogen atom or an alkyl or alkoxy radical containing up to 8 carbon atoms optionally substituted by one or more halogen atoms, or D forms with the carbon atom which carries it and one of the carbon atoms adjacent to it a carbon-carbon double bond, an epoxy radical, a cyclic hydrocarbonated radical, optionally substituted by one or more halogen atoms;

ii) when Y and W identical of different represent

where
e and f, identical or different, are a hydrogen atom, a halogen atom, a free, etherified or esterified hydroxyl radical, or an alkyl radical containing up to 8 carbon atoms optionally substituted by one or more halogen atoms;
X represents

where
g' is identical or different is a hydrogen atom, a halogen atom, a free, etherified or esterified hydroxyl radical, or an alkyl radical containing up to 8 carbon atoms optionally substituted by one or more halogen atoms or X represents a C=O radical, an oxygen atom or a nitrogen atom, or X forms with the carbon in the 2-position belonging to radical q an epoxy bridge, a cyclic hydrocarbonated radical optionally substituted by one or more halogen atoms; and
q represents a C= radical or a CD radical, in which D represents a hydrogen atom, a halogen atom or an alkyl or alkoxy radical containing up to 8 carbon atoms optionally substituted by one or more halogen atoms, or D forms with the carbon atom which carries it and one of the carbon atoms adjacent to it a carbon-carbon double bond, an epoxy radical, a cyclic hydrocarbonated radical, optionally substituted by one or more halogen atoms;
or
iii) Y and W identical or different represent

where
e and f, identical or different, are a hydrogen atom, a halogen atom, a free, etherified or esterified hydroxyl radical, or an alkyl radical containing up to 8 carbon atoms optionally substituted by one or more halogen atoms;
X represents

where
g and h identically or different represent a hydrogen atom, a halogen atom, a free etherified or esterified hydroxyl radical, or an alkyl radical containing up to 8 carbon atoms optionally substituted by one or more halogen atoms, or X represents a C=O radical, an oxygen atom or a nitrogen atom, or X forms with the carbon in position 2 belonging to radical q an epoxy bridge, a cyclic hydrocarbonated radical optionally substituted by one or more halogen atom; and
q represents a C= radical or a CD radical in which D represents a hydrogen atom, a halogen atom or an alkyl or alkoxy radical containing up to 8 carbon atoms optionally substituted by one or more halogen atoms, or D forms with the carbon atom which carries it and one of the carbon atoms adjacent to it a carbon-carbon double bond, an epoxy radical, a cyclic hydrocarbonated radical, optionally substituted by one or more halogen atoms;
n represents an integer varying from 0 to 8,
Z represents

in which
l and k, identical or different, represent a hydrogen atom, a halogen atom, a C≡N radical, a free, etherified or esterified hydroxyl radical, an SR' radical wherein R' is an organic group containing up to 8 carbon atoms or an alkyl radical containing up to 8 carbon atoms optionally substituted by one or more halogen atoms, or Z represents an oxygen, sulfur, nitrogen atom, a C=O or C=S radical, it being understood that if n is greater than 1, Z can take different values,
R represents an oxygen or sulfur atom;
$R_1$ and $R_2$, identical to or different from one another, represent a hydrogen atom, a linear, branched or cyclic, saturated or unsaturated, optionally substituted alkyl, CO-alkyl, CONH-alkyl or $CO_2$-alkyl radical, where said alkyl radical is optionally interrupted by one or more heteroatoms and contains up to 8 carbon atoms, or an optionally substituted aryl or heteroaryl radical;
the $-C-(Z)_n$ chain is fixed in position 3 or 4 of the benzamide, the dotted lines representing one or more optional double bonds, in all its possible isomeric forms as well as its mixtures
and an inert excipient.

4. A pesticidal composition for combating harmful arthropods and/or helminthes which comprises at least one compound of the formula
4-[(6-chloro-2-naphthalenyl)methyl]-N-(2-methylphenyl)benzamide,
4-[(5-bromo-2-naphthalenyl)methyl]-N-(2-methylphenyl)benzamide,
4-[(6-bromo-2-naphthalenyl)methyl]-N-(2-methylphenyl)benzamide,
4-[(6-bromo-3,4-dihydro-2-naphthalenyl)methyl]-N-(2-methylphenyl)benzamide,
4-[(6-chloro-1,2,3,4-tetrahydro-2-naphthalenyl)methyl]-N-(2-methylphenyl)benzamide,
4-[(6-chloro-3,4-dihydro-2-naphthalenyl)methyl]-N-(2-methylphenyl)benzamide,
4-[(6,7-dibromo-3,4-dihydro-2-naphthalenyl)methyl]-N-(2-methylphenyl)benzamide,
4-[(6,7-dibromo-2-naphthalenyl)methyl]-N-(2-methylphenyl)benzamide,
4-[(5,6-dichloro-1-fluoro-1,2,3,4-tetrahydro-2-naphthalenyl)methyl]-N-(2-methylphenyl)benzamide, 4-[(5,6-dichloro-3,4-dihydro-2-naphthalenyl)methyl]-N-(2-methylphenyl)benzamide, 4-[(6,7-dichloro-1,2,3,4-tetrahydro-2-naphthalenyl)methyl]-N-(2-methylphenyl)benzamide, 4-[(6,7-dichloro-2-naphthalenyl)methyl]-N-(2-methylphenyl)benzamide, 4-[(6,7-dichloro-2-naphthalenyl)methyl]-N-(2-dimethylpropyl)benzamide, 4-[(6-chloro-2-naphthalenyl)methyl]-N-(1,2-dimethylpropyl)benzamide.

5. A pesticidal composition for combating harmful athropods and/or helminthes which comprises at least one compound according to claim 2 and an inert carrier.

6. A compound of the formula

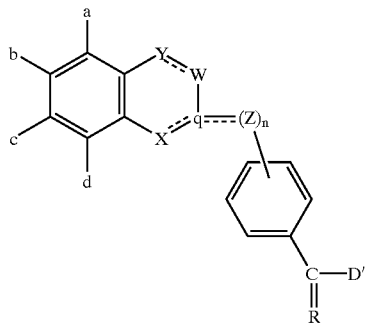

(II)

in which a, b, c and d, identical to or different from one another, represent a hydrogen atom, a halogen atom, an alkyl, alkenyl or alkynyl, O-alkyl, O-alkenyl or O-alkynyl, S-alkyl, S-alkenyl or S-alkynyl radical containing up to 8 carbon atoms, optionally substituted by one or more halogen atoms, a C≡N, $NO_2$ or $NH_2$ radical, the substituents a, b, c and d being able to form between themselves rings, which either contain or do not contain one or more hetero atoms, and which are substituted or unsubstituted, Y and W are identical to or different from one another, and both represent

in which e and f, identical or different, represent a hydrogen atom, a halogen atom, a free, etherified or esterified hydroxyl radical, or an alkyl radical containing up to 8 carbon atoms optionally substituted by one or more halogen atoms;

X represents

or

in which g, h and g', identical or different, represent a hydrogen atom, a halogen atom, a free, etherified or esterified hydroxyl radical, or an alkyl radical containing up to 8 carbon atoms optionally substituted by one or more halogen atoms, or X represents a C═O radical, an oxygen atom or a nitrogen atom, or X forms with the carbon in the 2-position belonging to radical q an epoxy bridge, a cyclic hydrocarbonated radical optionally substituted by one or more halogen atoms;

q represents a C═ radical or a CD radical, in which D represents a hydrogen atom, a halogen atom or an alkyl or alkoxy radical containing up to 8 carbon atoms optionally substituted by one or more halogen atoms, or D forms with the carbon atom which carries it and on eof the carbon atoms adjacent to it a carbon-carbon double bond, an epoxy radical, a cyclic hydrocarbonated radical, optionally substituted by one or more halogen atoms;

n represents an integer varying from 0 to 8,

Z represents

l and k, identical or different, represent a hydrogen atom, a halogen atom, a C≡N radical, a free, etherified or esterified hydroxyl radical, an SR' radical wherein R' is an organic group containing up to 8 carbon atoms or an alkyl radical containing up to 8 carbon atoms optionally substituted by one or more halogen atoms, or Z represents an oxygen, sulfur, nitrogen atom, C═O or C═S radical, it being understood that if n is greater than 1, Z can take different values, R represents an oxygen or sulfur atom; and D' represents an hydroxy radical, a halogen atom, an alkoxy radical containing up to 4 carbon atoms or a —P(O)(Oφ)NHφ group in which φ represents a phenyl group.

7. The pesticidal composition as defined in claim 3, in which Y represents a —$CH_2$— radical.

8. The pesticidal composition as defined in claim 3, in which Y and W represent a CH═ radical and together form a double bond in position 3(4).

9. The pesticidal composition as defined in claim 3, in which W represents a $CH_2$ radical.

10. The pesticidal composition as defined in claim 3, in which q and X represent a CH═ radical and together form a double bond.

11. The pesticidal composition as defined in claim 3, in which q represents a —CH— or C═ radical.

12. The pesticidal composition as defined in claim 3, in which X represents a $CH_2$ radical.

13. The pesticidal composition as defined in claim 3, in which X represents a

radical.

14. The pesticidal composition as defined in claim 3, in which Z represents a —CH$_2$— radical.

15. The pesticidal composition as defined in claim 3, in which n represents the number 1.

16. The pesticidal composition as defined in claim 3, in which R represents an oxygen atom.

17. The pesticidal composition as defined in claim 3, in which R$_1$ represents a hydrogen atom.

18. The pesticidal composition as defined in claim 3, in which R$_2$ represents an alkyl radical containing up to 8 carbon atoms or a phenyl radical optionally substituted by one or more halogen atoms and/or by one or more linear or branched alkyl radicals containing up to 8 carbon atoms.

19. The pesticidal composition as defined in claim 3, in which R$_2$ represents an alkyl radical containing up to 6 carbon atoms.

20. The pesticidal composition as defined in claim 3, in which R$_2$ represents a 2-methylphenyl radical.

21. The pesticidal composition as defined in claim 3, in which at least one of the substituents a, b, c or d represents a halogen atom.

22. The pesticidal composition as defined in claim 3, in which two of the substituent a, b, c and d represent a chlorine or bromine atom.

23. The pesticidal composition as defined in claim 21, which two of the substituents a, b, c and d represent a hydrogen atom.

24. A method for combatting and/or eradicating infestations of pests in an animal, plant or stored product which comprises administering to said animal or applying to said plant or stored product or to a locality where said plant or stored product resides, an effective amount of a compound of the formula

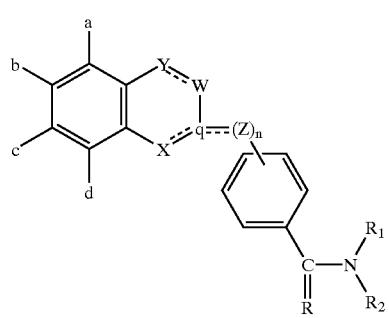

(I)

in which
   a, b, c, and d, identical to or different from one another, represent a hydrogen atom, a halogen atom, an alkyl, alkenyl or alkynyl, O-alkyl, O-alkenyl or O-alkynyl, S-alkyl, S-alkenyl or S-alkynyl radical containing up to 8 carbon atoms, optionally substituted by one or more halogen atoms, a C≡N, NO$_2$ or NH$_2$ radical, the substituents a, b, c, and d being able to form between themselves rings, which either contain or do not contain one or more hetero atoms, and which are substituted or unsubstituted;
   Y and W, identical to or different from one another, both represent

or both represent

in which
   e, f, and e', identical or different, represent a hydrogen atom, a halogen atom, a free, etherified or esterified hydroxyl radical, or an alkyl radical containing up to 8 carbon atoms optionally substituted by one or more halogen atoms;
   X represents

or

in which
   g, h, g', identical or different, represent a hydrogen atom, a halogen atom, a free, etherified or esterified hydroxyl radical, or an alkyl radical containing up to 8 carbon atoms optionally substituted by one or more halogen atoms, or X represents a C=O radical, an oxygen atom or a nitrogen atom, or X forms with the carbon in 2-postion belonging to radical q an epoxy bridge, a cyclic hydrocarbonated radical optionally substituted by one or more halogen atoms;
   q represents a C= radical or a CD radical, in which D represents a hydrogen atom, a halogen atom or an alkyl or alkoxy radical containing up to 8 carbon atoms optionally substituted by one or more halogen atoms, or D forms with carbon atom which carries it and one of the carbon atoms adjacent to it a carbon-carbon double bond, an epoxy radical, a cyclic hydrocarbonated radical, optionally substituted by one or more halogen atoms;
   n represents an integer varying from 0 to 8,
   Z represents

in which l and k, identical
   or different, represent a hydrogen atom, a halogen atom, a C≡N radical, a free, etherified or esterified hydroxyl radical, an SR' radical wherein R' is an organic group containing up to 8 carbon atoms or an alkyl radical containing up to 8 carbon atoms optionally substituted by one or more halogen atoms, or Z represents an oxygen, sulfur, nitrogen atom, a C=O or C=S radical, it being understood that if n is greater than 1, Z can take different values, R represents an oxygen or sulfur atom;

$R_1$ and $R_2$, identical to or different from one another, represent a hydrogen atom, a linear, branched or cyclic, saturated or unsaturated, optionally substituted alkyl, CO-alkyl, CONH-alkyl or $CO_2$ alkyl radical, said alkyl radical, optionally interrupted by one or more heteroatoms and containing up to 8 carbon atoms, or an optionally substituted aryl or heteroaryl radical, the —C—$(Z)_n$ chain is fixed in position 3 or 4 of the benzamide, the dotted lines representing one or more optional double bonds, in all its possible isomeric forms as well as its mixtures wherein at least one of the substituents a, b, c or d represents a halogen atom, whereby said pest is an anthropod, helminth, mollusk a combination of at least two of the the foregoing.

25. A compound of the formula

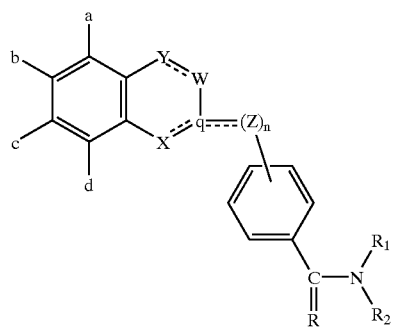

(I)

in which a, b, c and d, identical to or different from one another, represent a hydrogen atom, a halogen atom, an alkyl, alkenyl or alkynyl, O-alkyl, O-alkenyl or O-alkynyl, S-alkyl, S-alkenyl or S-alkynyl radical containing up to 8 carbon atoms, optionally substituted by one or more halogen atoms, a C≡N, $NO_2$ or $NH_2$ radical, the substituents a, b, c and d being able to form between themselves rings, which either contain or do not contain one or more hetero atoms, and which are substituted or unsubstituted, Y and W are identical to or different from one another, and both represent

in which e, f, and e', identical or different, represent a hydrogen atom, a halogen atom, a free, etherified or esterified hydroxyl radical, or an alkyl radical containing up to 8 carbon atoms optionally substituted by one or more halogen atoms;

X represents

or

in which g, h and g', identical or different, represent a hydrogen atom, a halogen atom, a free, etherified or esterified hydroxyl radical, or an alkyl radical containing up to 8 carbon atoms optionally substituted by one or more halogen atoms, or X represents a C=O radical, an oxygen atom or a nitrogen atom, or X forms with the carbon in the 2-position belonging to radical q an epoxy bridge, a cyclic hydrocarbonated radical optionally substituted by one or more halogen atoms;

q represents a C= radical or a CD radical, in which D represents a hydrogen atom, a halogen atom or an alkyl or alkoxy radical containing up to 8 carbon atoms optionally substituted by one or more halogen atoms, or D forms with the carbon atom which carries it and on eof the carbon atoms adjacent to it a carbon-carbon double bond, an epoxy radical, a cyclic hydrocarbonated radical, optionally substituted by one or more halogen atoms;

n represents an integer varying from 0 to 8,

Z represents

in which l and k, identical or different, represent a hydrogen atom, a halogen atom, a C≡N radical, a free, etherified or esterified hydroxyl radical, an SR' radical wherein R' is an organic group containing up to 8 carbon atoms or an alkyl radical containing up to 8 carbon atoms optionally substituted by one or more halogen atoms, or Z represents an oxygen, sulfur, nitrogen atom, C=O or C=S radical, it being understood that if n is greater than 1, Z can take different values, R represents an oxygen or sulfur atom;

$R_1$ and $R_2$ identical to or different from one another, represent a hydrogen atom, a linear, branched or cyclic, saturated or unsaturated, optionally substituted alkyl, CO-alkyl, CONH-alkyl or $CO_2$ alkyl radical, said alkyl radical optionally interrupted by one or more heteroatoms, containing up to 8 carbon atoms, or an optionally substituted aryl or heteroaryl radical, the —C—$(Z)_n$ chain is fixed in position 3 or 4 of the benzamide, the dotted lines representing one or more optional double bonds.

26. The compound(s) as defined in claim 25, which Y represents a —$CH_2$— radical.

27. A process for the preparation of compounds of formula (I) defined in claim 25 which comprises reacting a compound of formula (II):

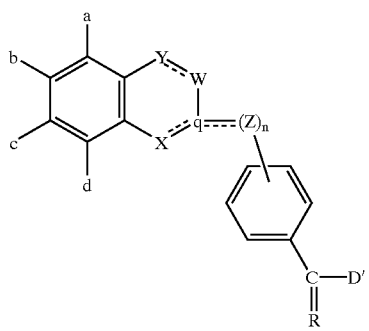
(II)

in which
a, b, c, d, X, Y, W, Q, Z, n, and R are defined as in formula (I) in claim 25 and D' represents a hydroxy radical, a halogen atom, an alkoxy radical containing up to 4 carbon atoms or a —P(O)(Oφ)NHφ group in which φ represents a phenyl group, with a compound of formula (III):

in which
R₁ and R₂, identical to or different from one another, represent a hydrogen atom, a linear, branched or cyclic, saturated or unsaturated, optionally substituted alkyl, CO-alkyl, CONH-alkyl or CO₂-alkyl radical, where said alkyl radical is optionally interrupted by one or more heteroatoms and contains up to 8 carbon atoms, or an optionally substituted aryl or heteroaryl radical;
in order to form the corresponding compound of formula (I).

28. A method for combatting and/or eradicating infestations of pests in an animal, plant or stored product which comprises administering to said animal or applying to said plant or stored product or to a locality when aid plant or stored product resides, an effective amount of a compound according to claim 25, whereby said pest is an arthropod, helminth, mollusk, or a combination of at least two of the foregoing.

29. A method for protecting crops or treating premises used for storing said crops from insects, acarides and nematodes which comprises applying to said crops or to said premises an effective amount of a compound of the formula

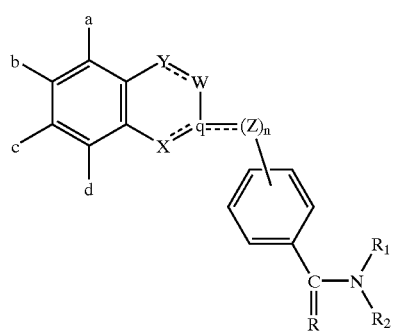
(I)

in which
a, b, c, and d, identical to or different from one another, represent a hydrogen atom, a halogen atom, an alkyl, alkenyl or alkynyl, O-alkyl, O-alkenyl or O-alkynyl, S-alkyl, S-alkenyl or S-alkynyl radical containing up to 8 carbon atoms, optionally substituted by one or more halogen atoms, a C≡N, NO₂ or NH₂ radical, the substituents a, b, c, and d being able to form between themselves rings, which either contain or do not contain one or more hetero atoms, and which are substituted or unsubstituted, Y and W, identical to or different from one another,

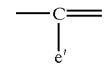

both represent

in which
e, f, and e', identical or different, represent a hydrogen atom, a halogen atom, a free, etherified or esterified hydroxyl radical, or an alkyl radical containing up to 8 carbon atoms optionally substituted by one or more halogen atoms;

X represents

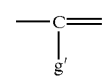

or

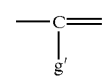

in which
g, h, g', identical or different, represent a hydrogen atom, a halogen atom, a free, etherified or esterified hydroxyl radical, or an alkyl radical containing up to 8 carbon atoms optionally substituted by one or more halogen atoms, or X represents a C=O radical, an oxygen atom or a nitrogen atom, or X forms with the carbon in 2-position belonging to radical q an epoxy bridge, a cyclic hydrocarbonated radical optionally substituted by one or more halogen atoms;

g represents a C= radical or a CD radical, in which D represents a hydrogen atom, a halogen atom or an alkyl or alkoxy radical containing up to 8 carbon atoms optionally substituted by one or more halogen atoms, or D forms with carbon atom which carries it and one of the carbon atoms adjacent to it a carbon-carbon double bond, an epoxy radical, a cyclic hydrocarbonated radical, optionally substituted by one or more halogen atoms;

n represents an integer varying from 0 to 8,

Z represents

in which l and k, identical or different, represent a hydrogen atom, a halogen atom, a C≡N radical, a free, etherified or esterified hydroxyl radical, an SR' radical wherein R' is an organic group containing up to 8 carbon atoms or an alkyl radical containing up to 8 carbon atoms optionally substituted by one or more halogen atoms, or Z represents an oxygen, sulfur, nitrogen atom, a C=O or C=S radical, it being understood that if n is greater than 1, Z can take different values, R represents an oxygen or sulfur atom;

$R_1$ and $R_2$, identical to or different from one another, represent a hydrogen atom, a linear, branched or cyclic, saturated or unsaturated, optionally substituted alkyl, CO-alkyl, CONH-alkyl or $CO_2$ alkyl radical, said alkyl radical, optionally interrupted by one or more heteroatoms and containing up to 8 carbon atoms, or an optionally substituted aryl or heteroaryl radical, the —C—$(Z)_n$ chain is fixed in position 3 or 4 of the benzamide, the dotted lines representing one or more optional double bonds, in all its possible isomeric forms as well as mixtures of said forms.

* * * * *